(12) United States Patent
Tay et al.

(10) Patent No.: US 12,345,784 B2
(45) Date of Patent: Jul. 1, 2025

(54) PORTABLE HANDHELD MAGNETIC PARTICLE IMAGING

(71) Applicant: Agency for Science, Technology and Research, Singapore (SG)

(72) Inventors: Zhi Wei Tay, Singapore (SG); Teck Hock Lee, Sg (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 136 days.

(21) Appl. No.: 18/005,947

(22) PCT Filed: Jul. 19, 2021

(86) PCT No.: PCT/SG2021/050424
§ 371 (c)(1),
(2) Date: Jan. 18, 2023

(87) PCT Pub. No.: WO2022/019835
PCT Pub. Date: Jan. 27, 2022

(65) Prior Publication Data
US 2023/0280421 A1  Sep. 7, 2023

(30) Foreign Application Priority Data
Jul. 20, 2020  (SG) .............................. 10202006890P

(51) Int. Cl.
*G01R 33/12*  (2006.01)
*A61B 5/00*  (2006.01)
(Continued)

(52) U.S. Cl.
CPC ........ *G01R 33/1276* (2013.01); *A61B 5/0035* (2013.01); *A61B 5/0515* (2013.01);
(Continued)

(58) Field of Classification Search
CPC ............ G01R 33/1276; G01R 33/0047; G01R 33/022; A61B 5/0035; A61B 5/0515; A61B 2560/0431; A61B 2562/0223; A61B 5/067
See application file for complete search history.

(56) References Cited

U.S. PATENT DOCUMENTS 6,198,564 B1 *  3/2001  Knight .................. F41G 7/2253
250/236
2009/0281416 A1   11/2009  Gleich et al.
(Continued)

FOREIGN PATENT DOCUMENTS

CN   107462847 A   12/2017
WO   2009/104151 A2   8/2009

OTHER PUBLICATIONS

Tay, Z.W., Goodwill, P.W., Hensley, D., Taylor, L.A., Zheng, B., & Conolly, S.M. (2016). A High-Throughput, Arbitrary-Waveform, MPI Spectrometer and Relaxometer for Comprehensive Magnetic Particle Optimization and Characterization. Scientific Reports, 6. (Year: 2016).*

(Continued)

*Primary Examiner* — Yi-Shan Yang
*Assistant Examiner* — Nicholas A Robinson
(74) *Attorney, Agent, or Firm* — Mark H. Whittenberger; Holland & Knight LLP

(57) ABSTRACT

This invention relates to a portable magnetic particle imaging (MPI) device. The portable MPI device comprises a handheld probe and a processing unit. The handheld probe comprises a main housing a first sensor coil, a second sensor coil, a transmitter coil arranged between the first and second sensor coils, and an excitation priming frame housing magnetic component and the processing unit comprises a transmitter communicatively connected to the transmitter coil
(Continued)

and the excitation priming frame, a receiver communicatively connected to the first and second sensor coils.

16 Claims, 37 Drawing Sheets

(51) Int. Cl.
  *A61B 5/0515* (2021.01)
  *G01R 33/00* (2006.01)
(52) U.S. Cl.
  CPC .. *G01R 33/0047* (2013.01); *A61B 2560/0431* (2013.01); *A61B 2562/0223* (2013.01)

(56) References Cited

U.S. PATENT DOCUMENTS

| | | | |
|---|---|---|---|
| 2012/0229130 A1* | 9/2012 | Hattersley | G01R 33/1215 324/248 |
| 2014/0266174 A1 | 9/2014 | Hattersley et al. | |
| 2015/0276902 A1 | 10/2015 | Weaver et al. | |
| 2017/0067972 A1 | 3/2017 | Diamond et al. | |
| 2017/0340311 A1* | 11/2017 | Shiki | A61B 8/483 |
| 2019/0101604 A1* | 4/2019 | Buzug | H01F 7/0278 |
| 2023/0280421 A1* | 9/2023 | Tay | G01R 33/022 600/409 |

OTHER PUBLICATIONS

Lu, Ming-Chen et al. "Backward-mode ultrafast pulsed magnetomotive ultrasound." 2017 IEEE International Ultrasonics Symposium (IUS) (2017): 1-4. (Year: 2017).*

International Search Report and Written Opinion issued in Application Serial No. PCT/SG2021/050424 on Nov. 2, 2021.

Tay Z. W. et al., A High-Throughput, Arbitrary-Waveform, MPI Spectrometer and Relaxometer for Comprehensive Magnetic Particle Optimization and Characterization. Scientific Reports, Sep. 30, 2016, vol. 6 No. 34180, pp. 1-12. [Retrived on Oct. 22, 2021] <DOI: 10.1038/SREP34180>.

Extended European Search Report and Written Opinion issued in related Application Serial No. 21845660.6 on Jul. 22, 2024.

Search Report issued in related Singapore Application Serial No. 11202300098W on Jun. 18, 2024.

* cited by examiner

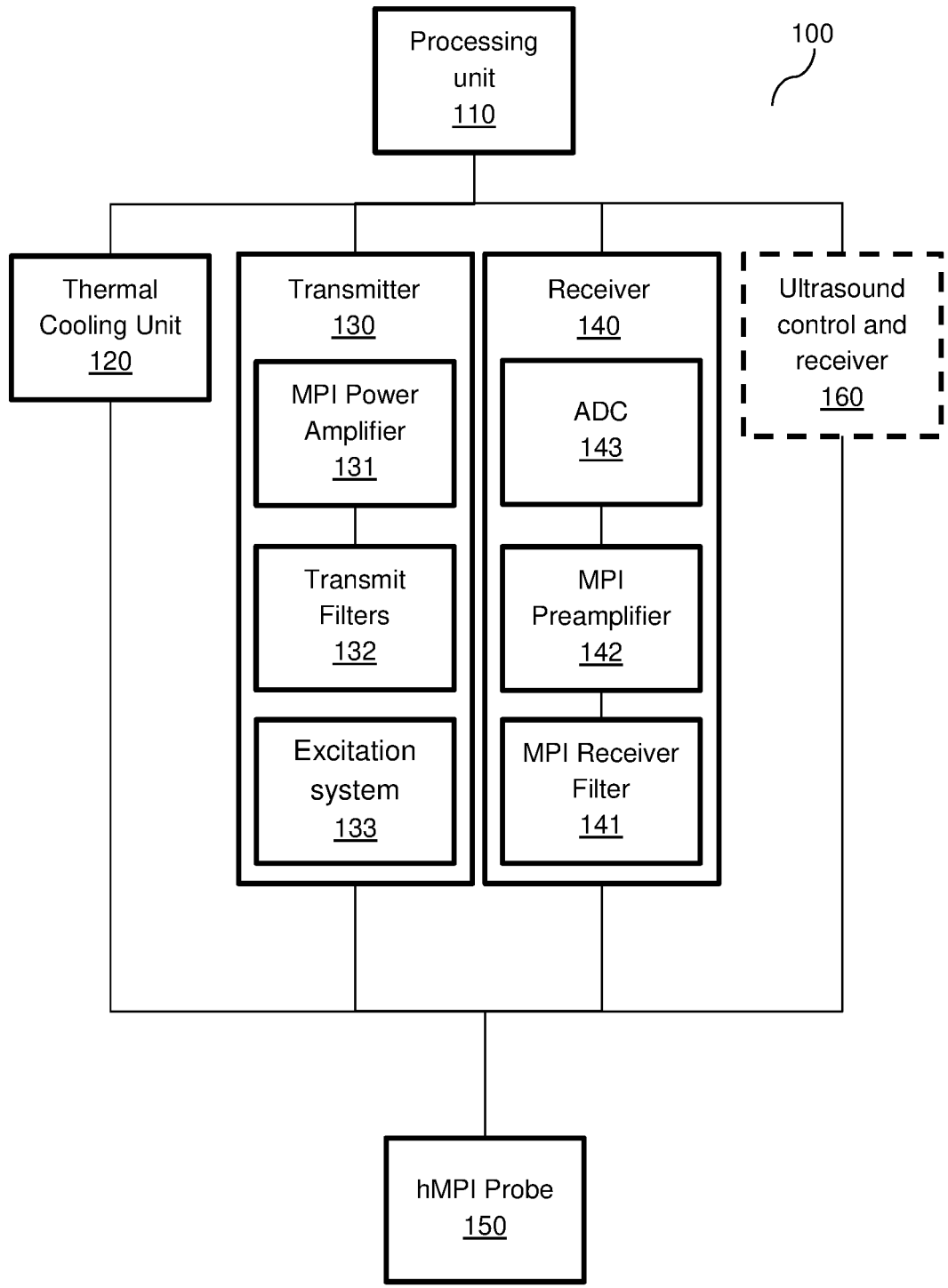
Figure 1.1

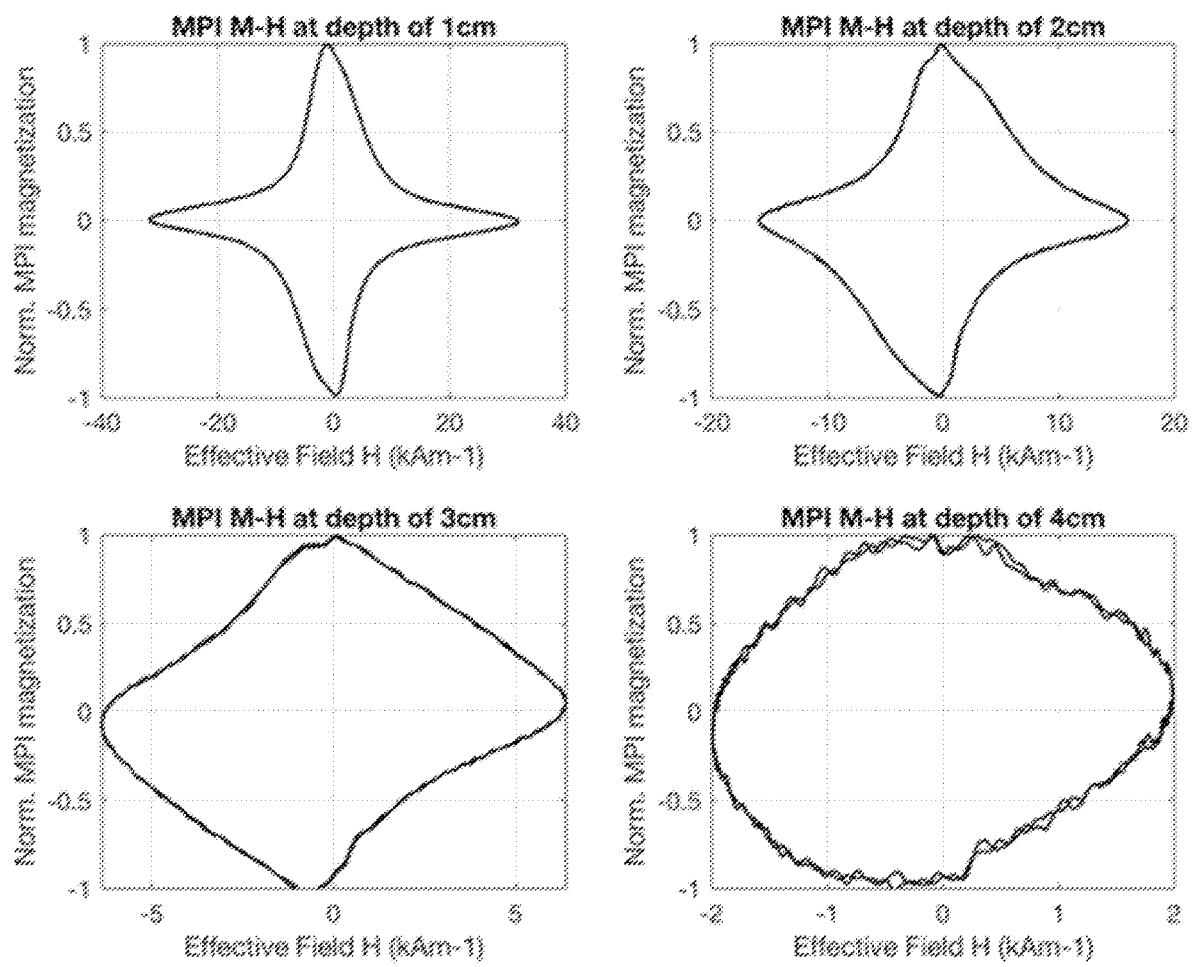
Figure 1.2

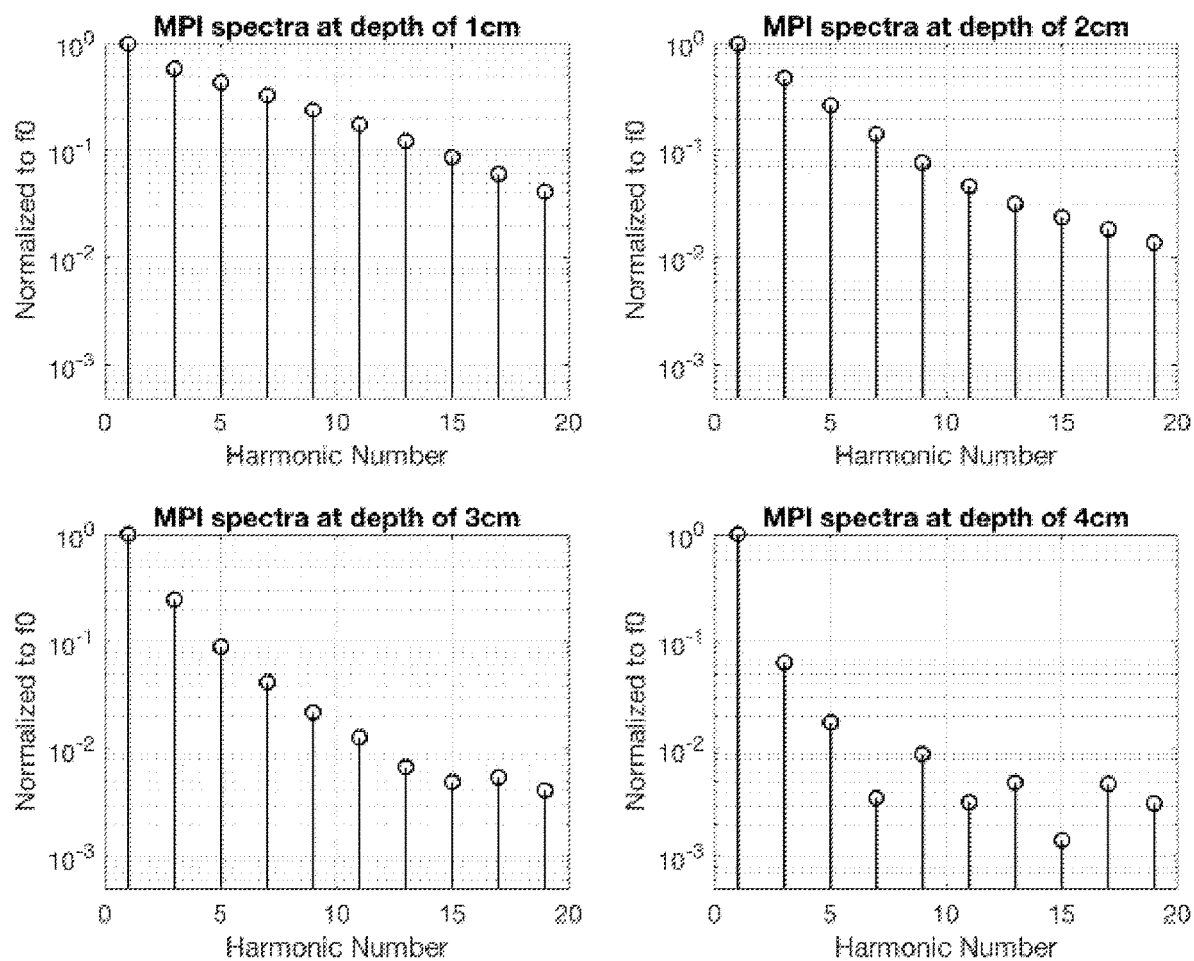
Figure 1.3

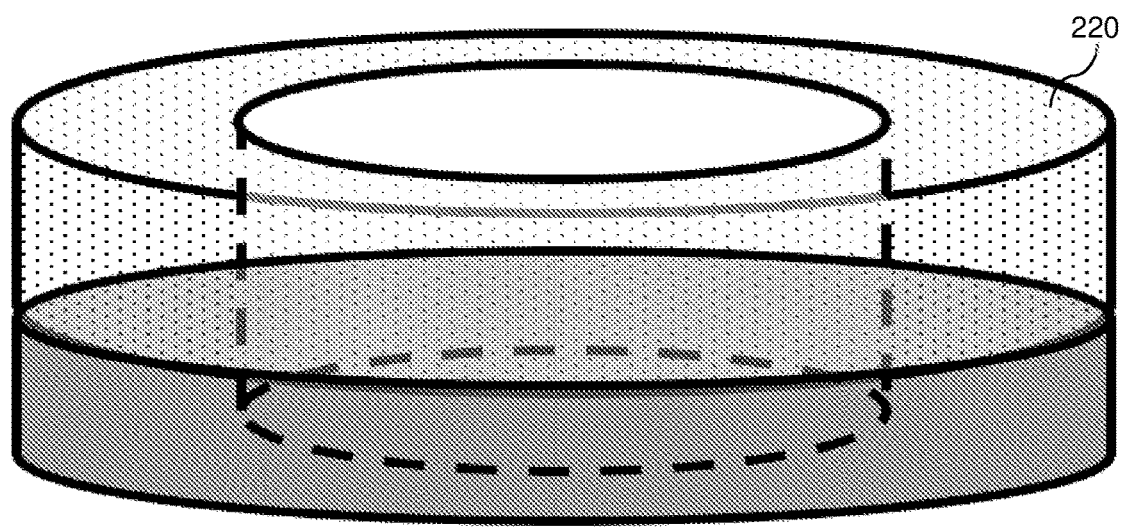
Figure 6
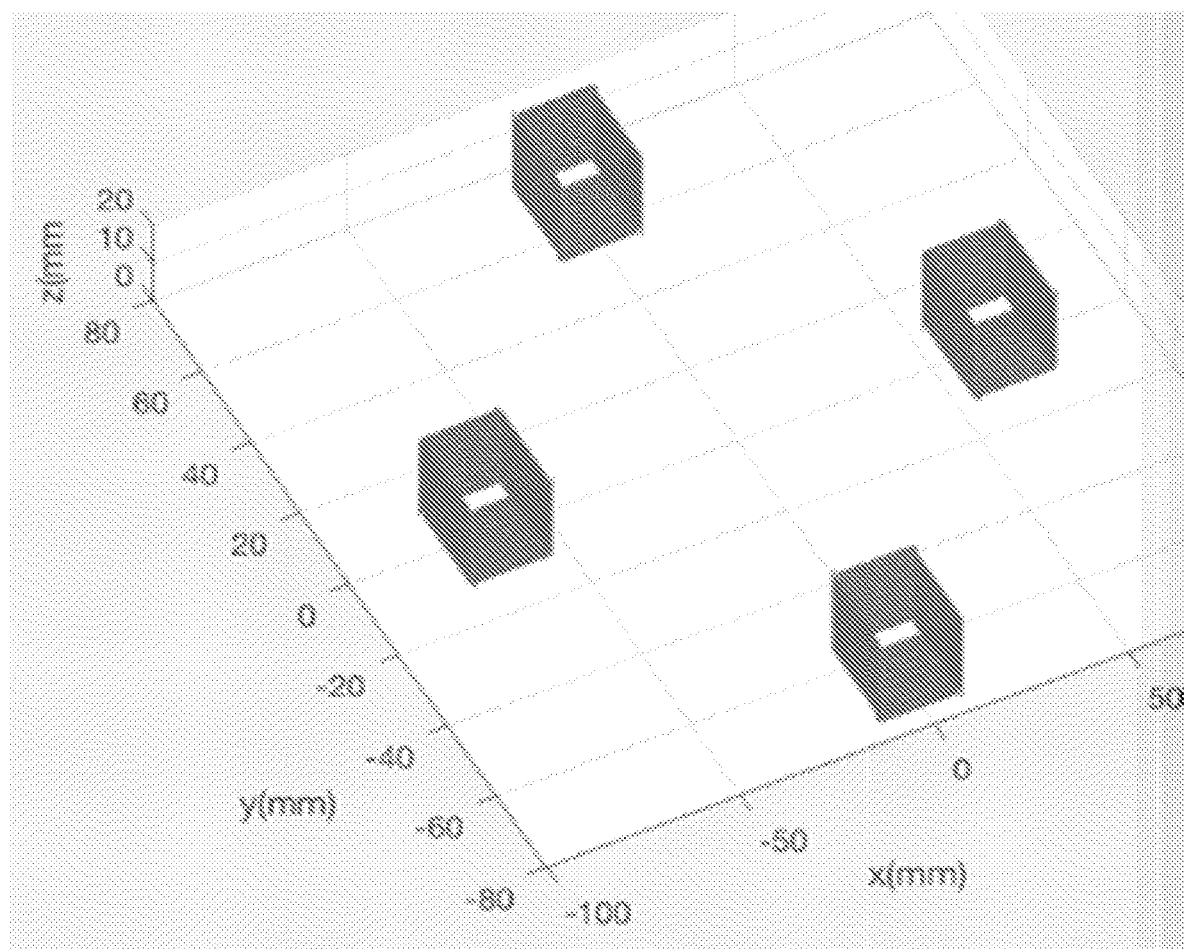
Figure 7.1

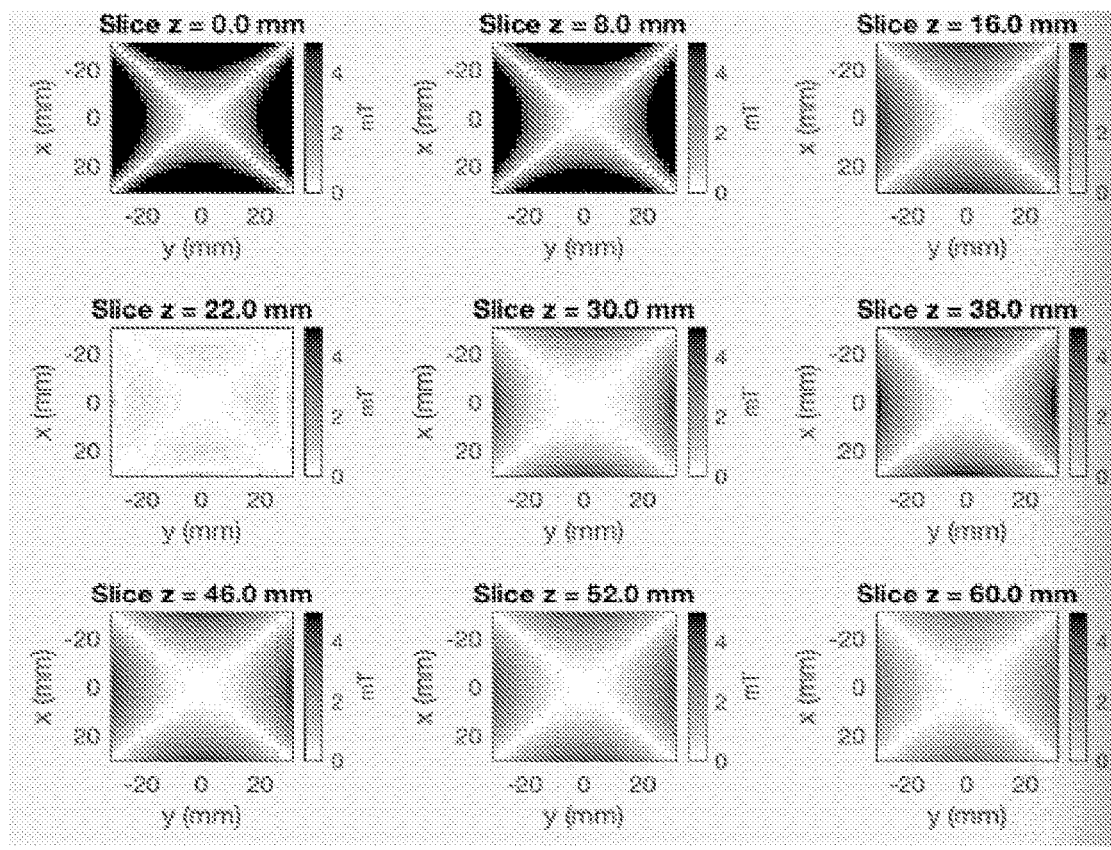
Figure 7.2
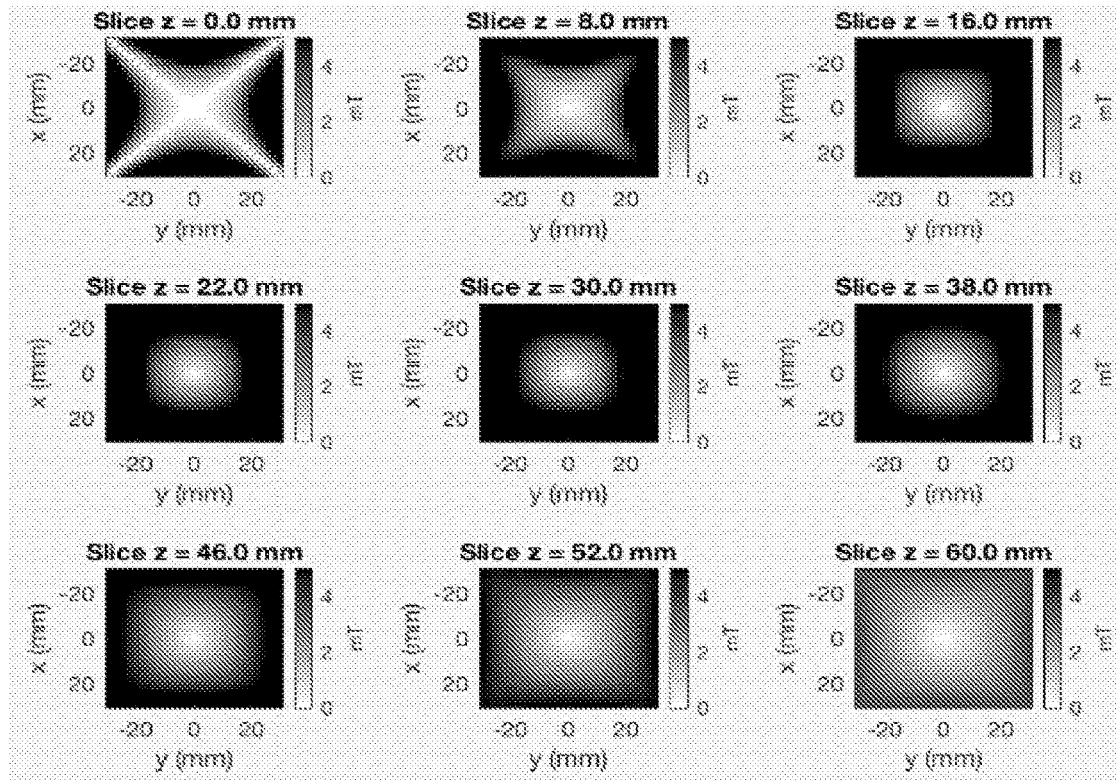
Figure 7.3

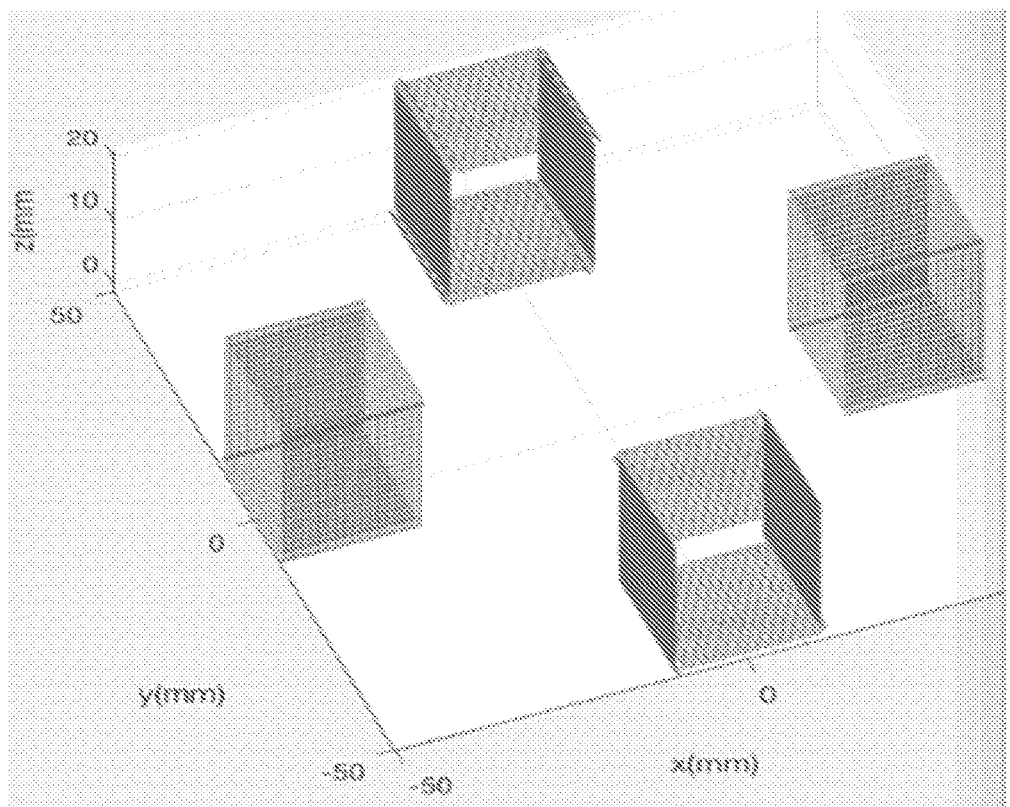
Figure 8.1
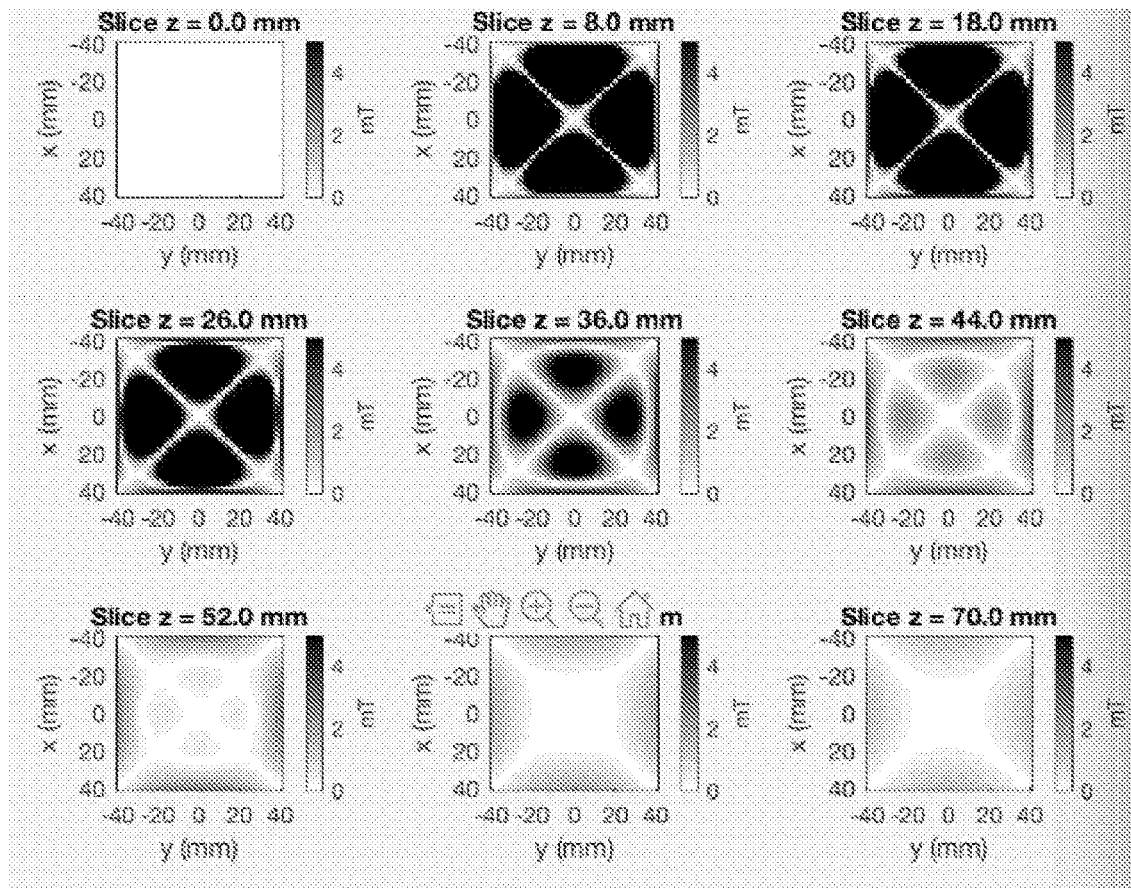
Figure 8.2

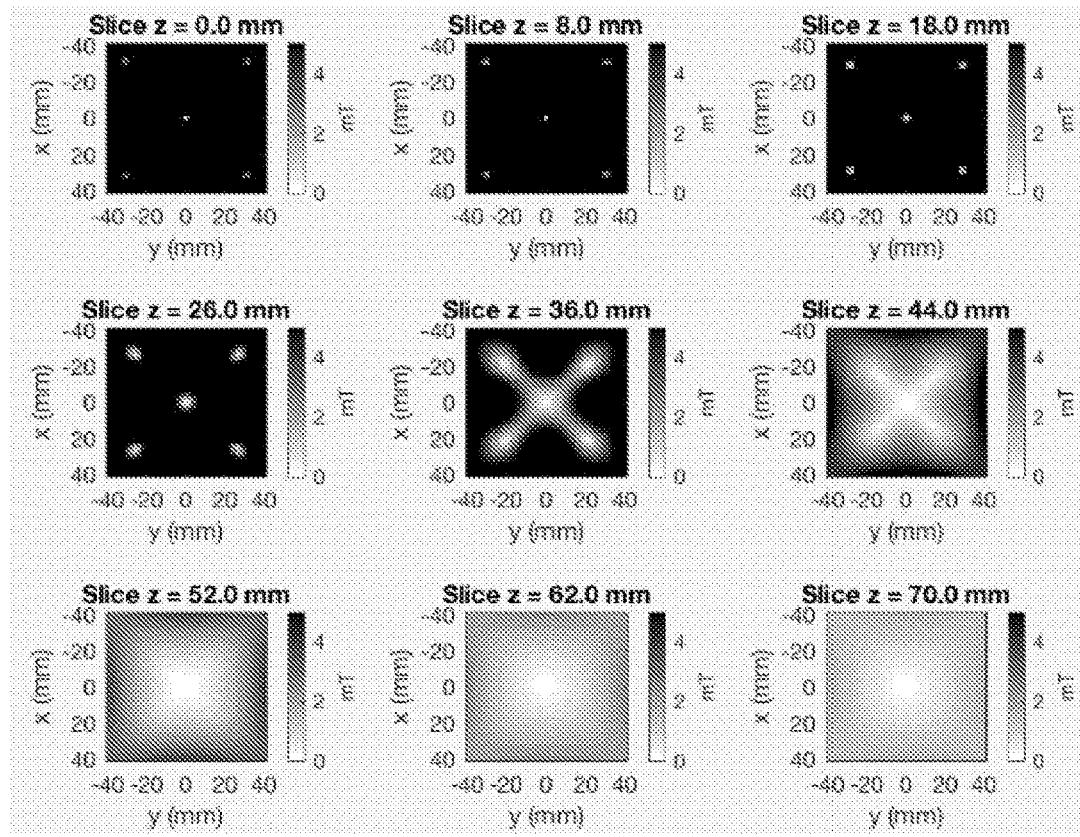
Figure 8.3
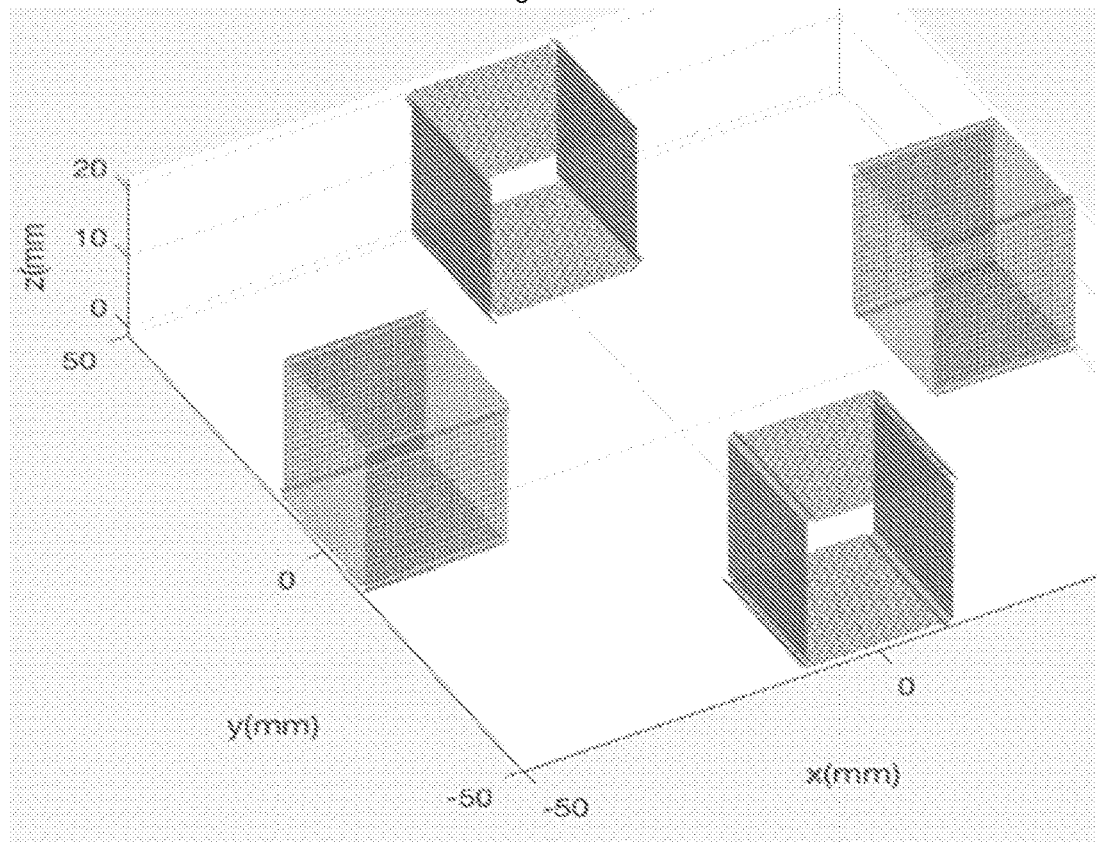
Figure 9.1

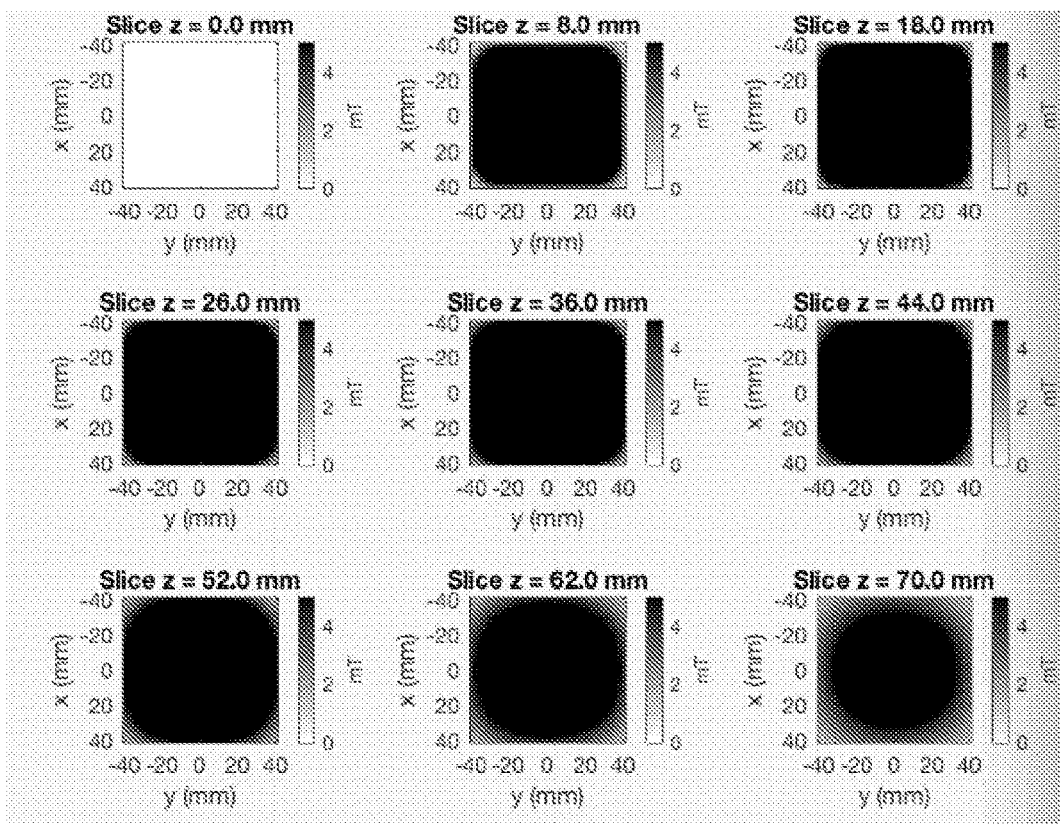
Figure 9.2
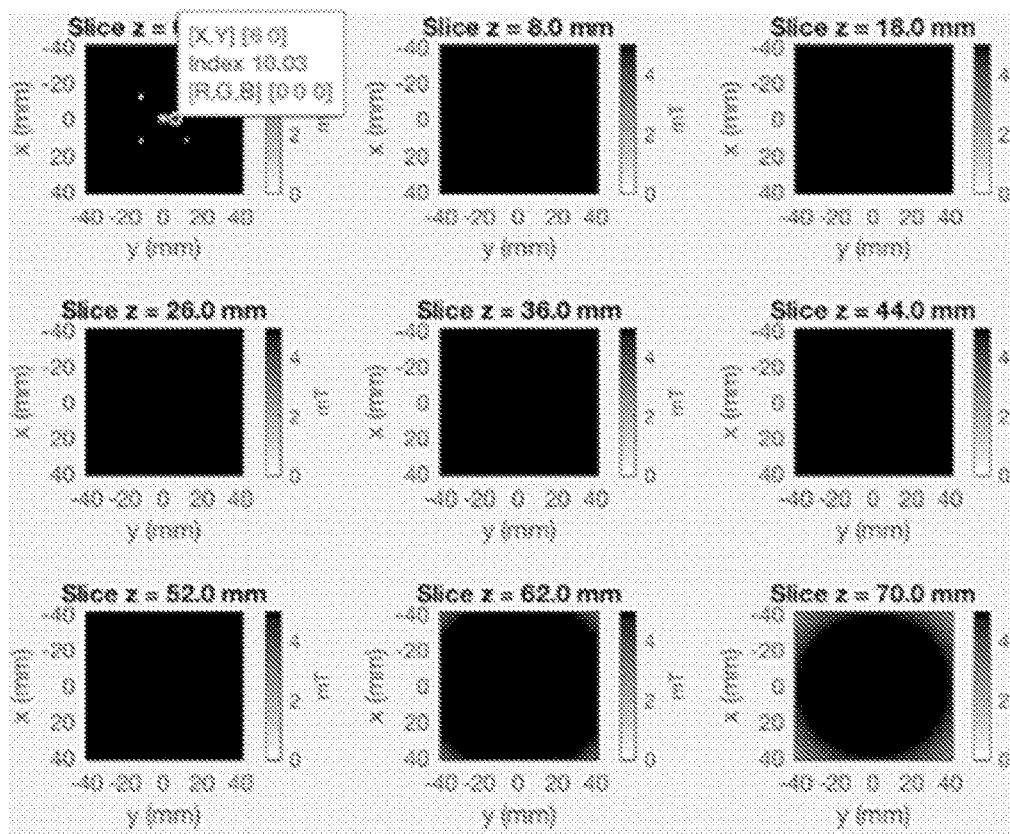
Figure 9.3

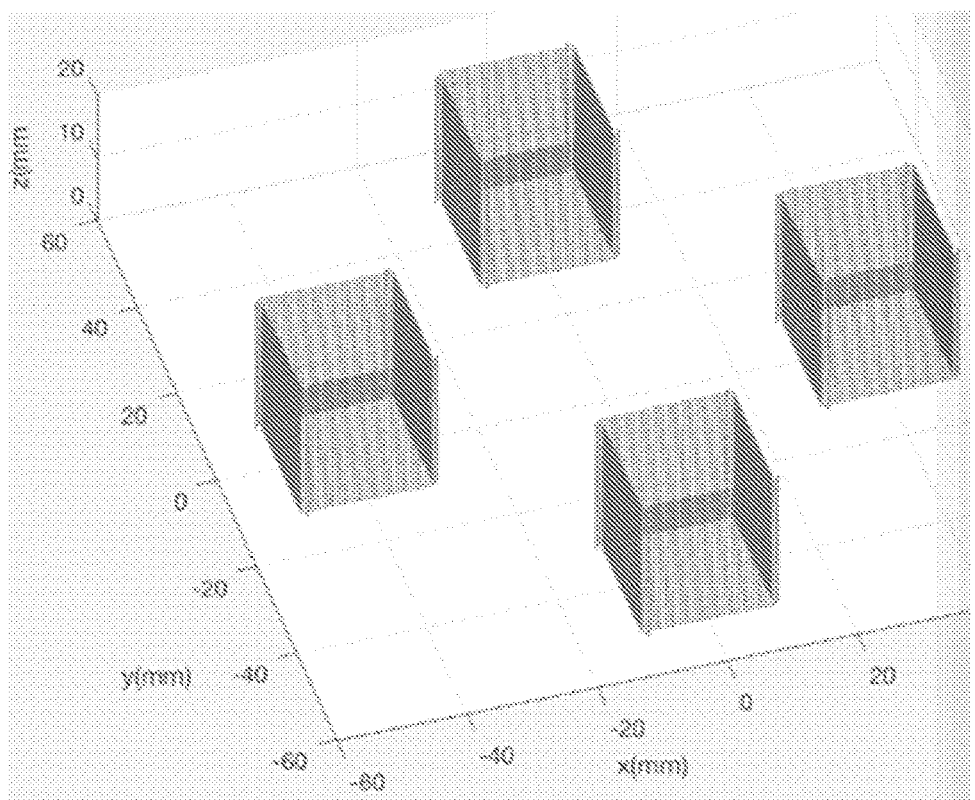
Figure 10.1
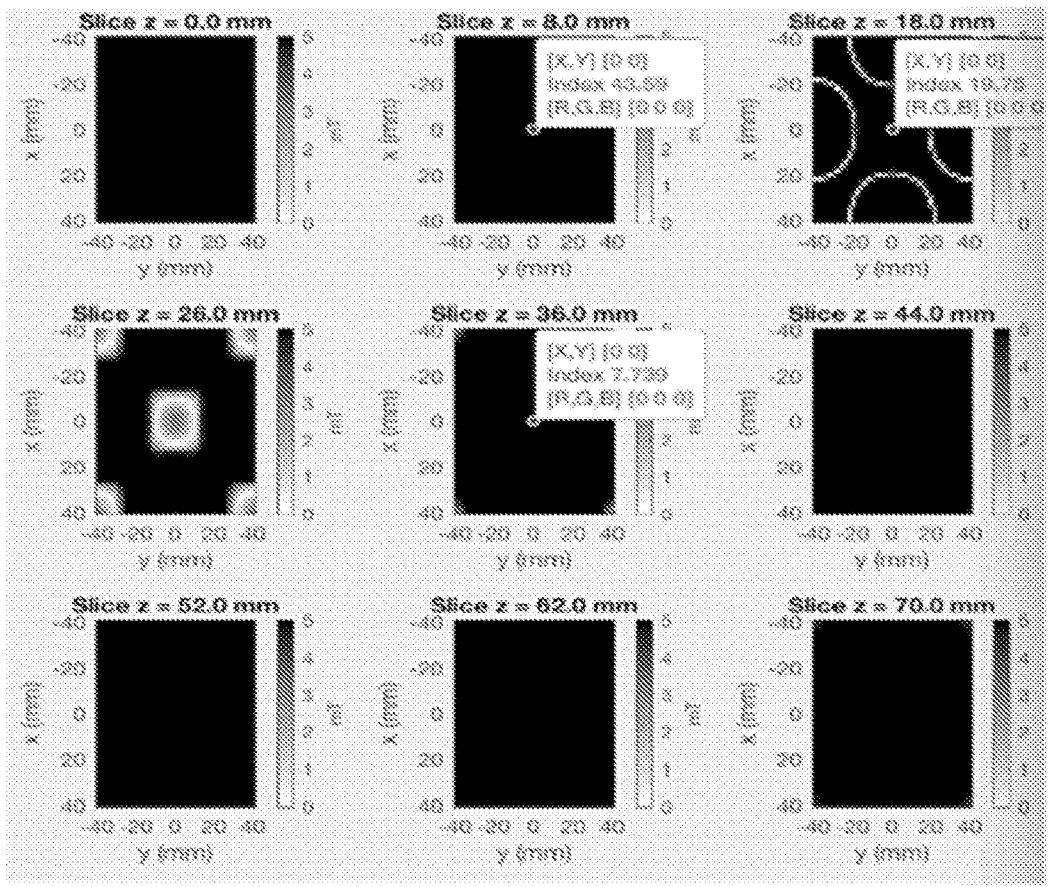
Figure 10.2

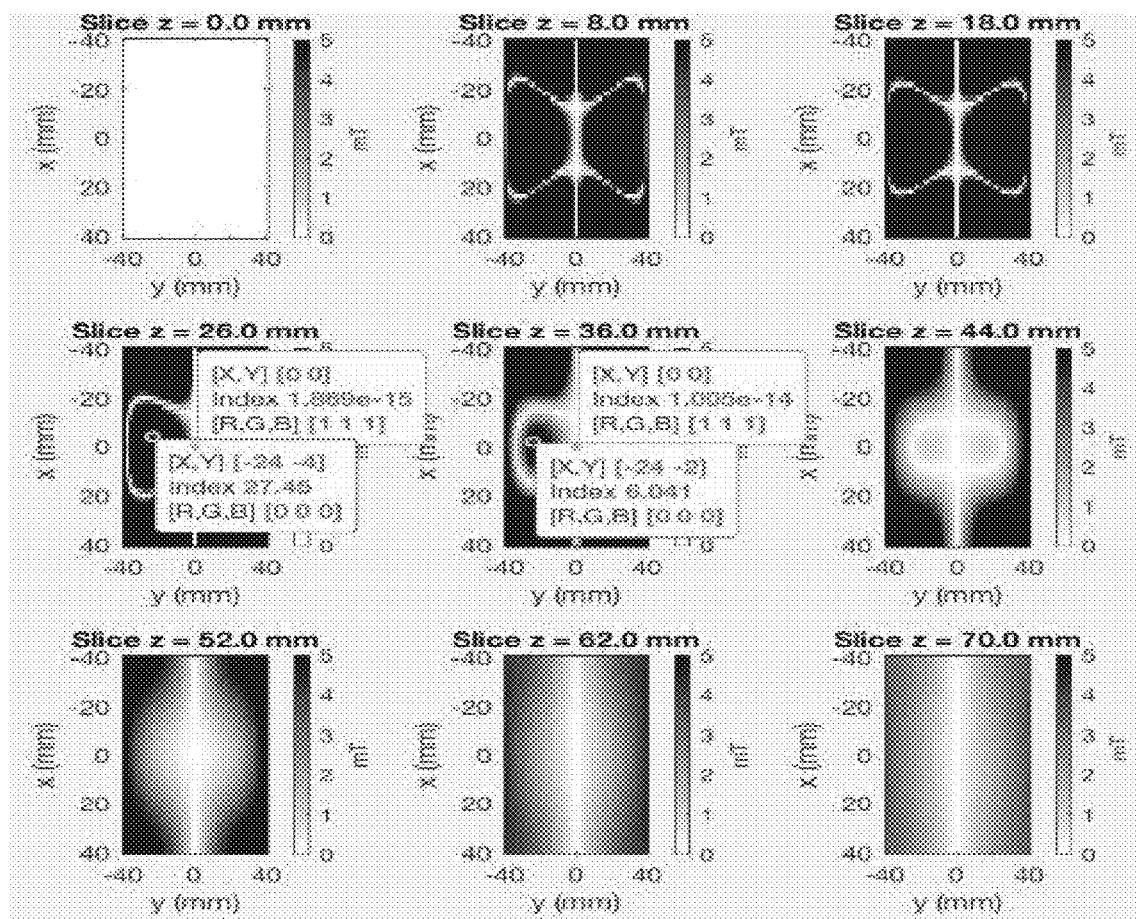
Figure 10.3

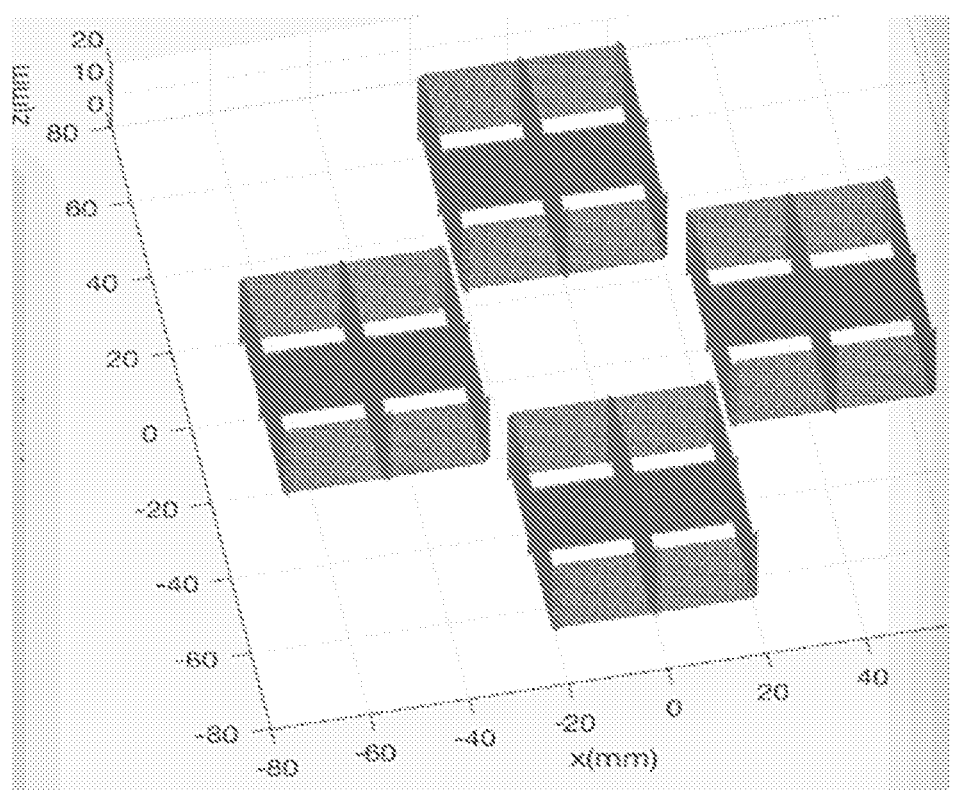
Figure 11.1

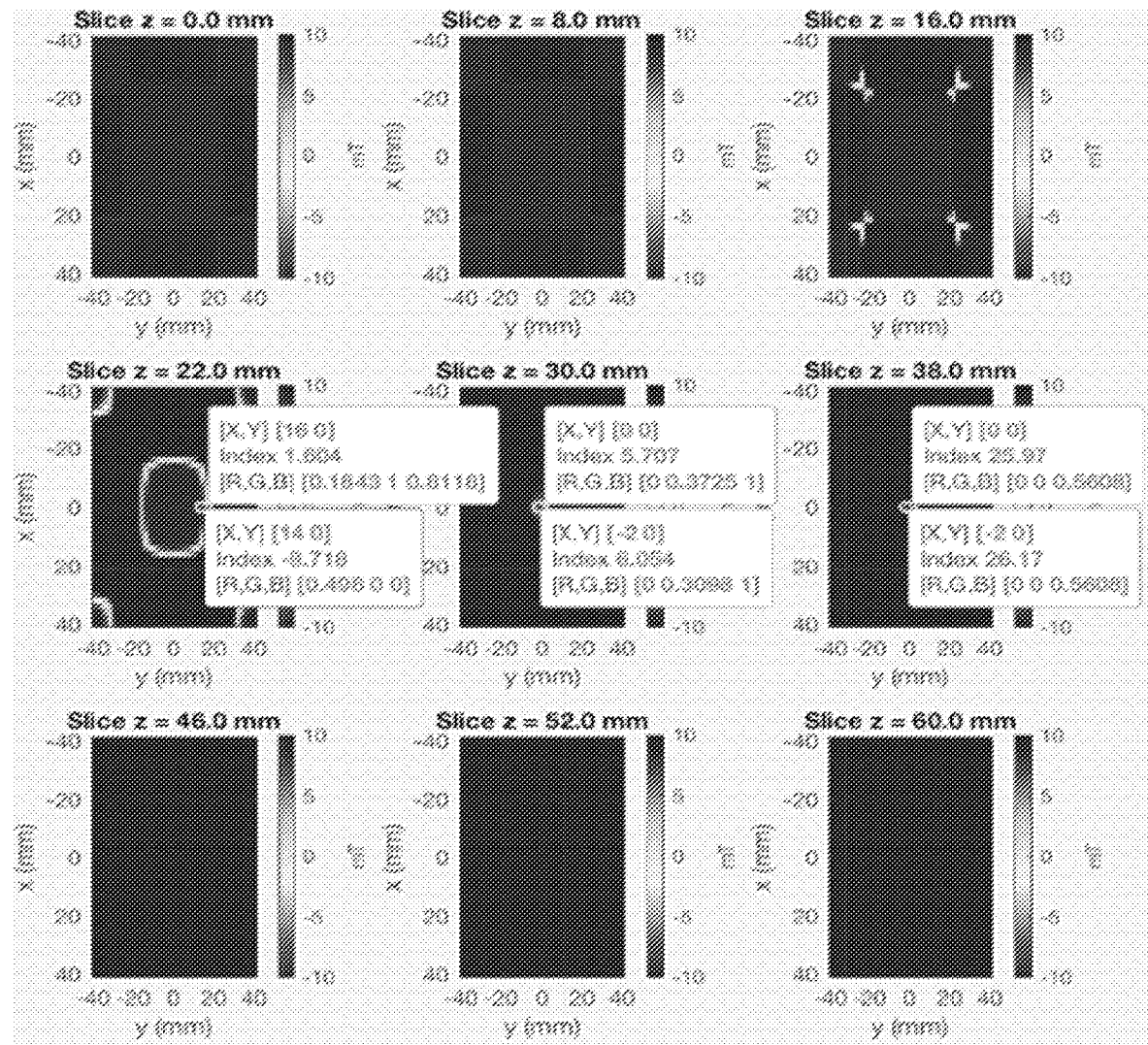
Figure 11.2

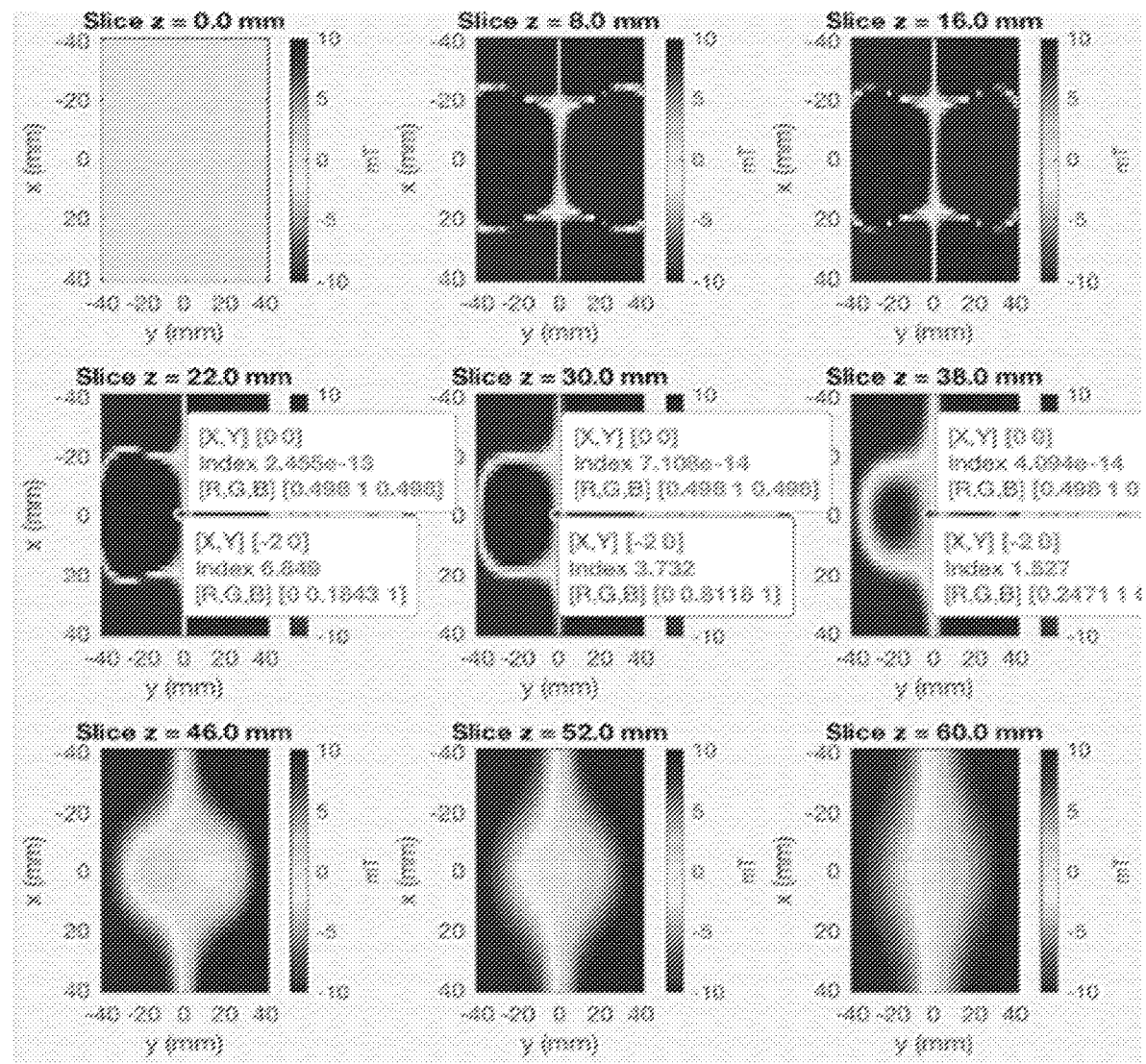
Figure 11.3

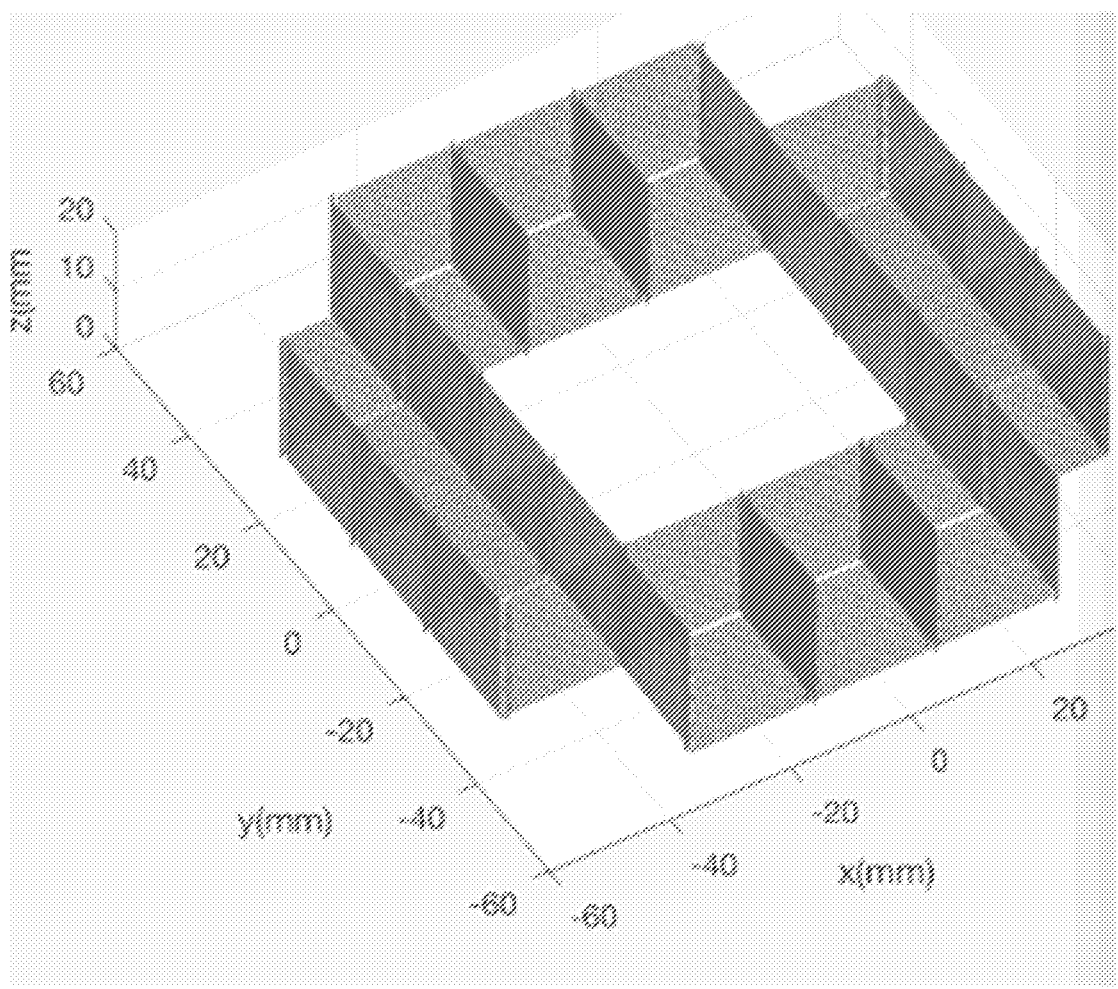
Figure 12.1

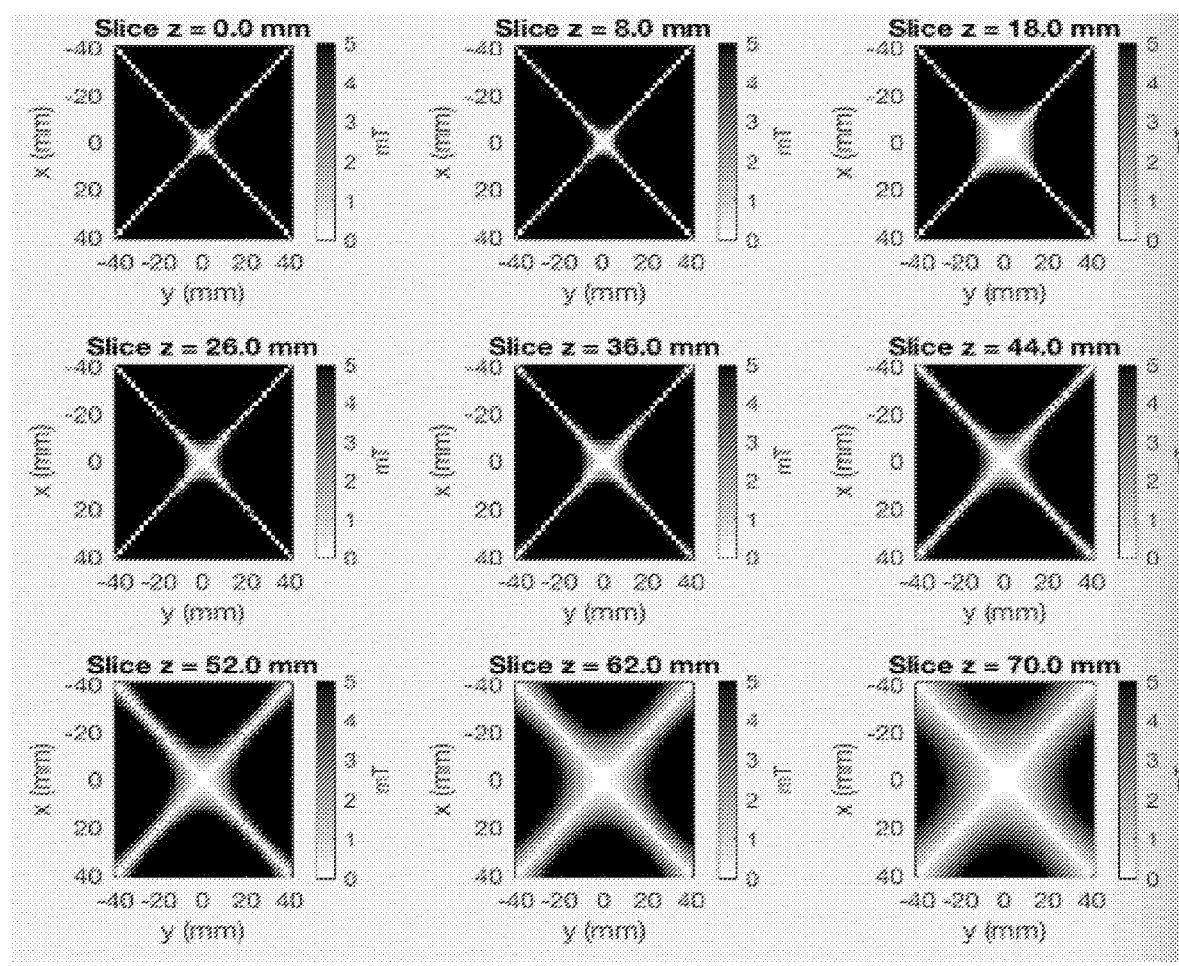
Figure 12.2

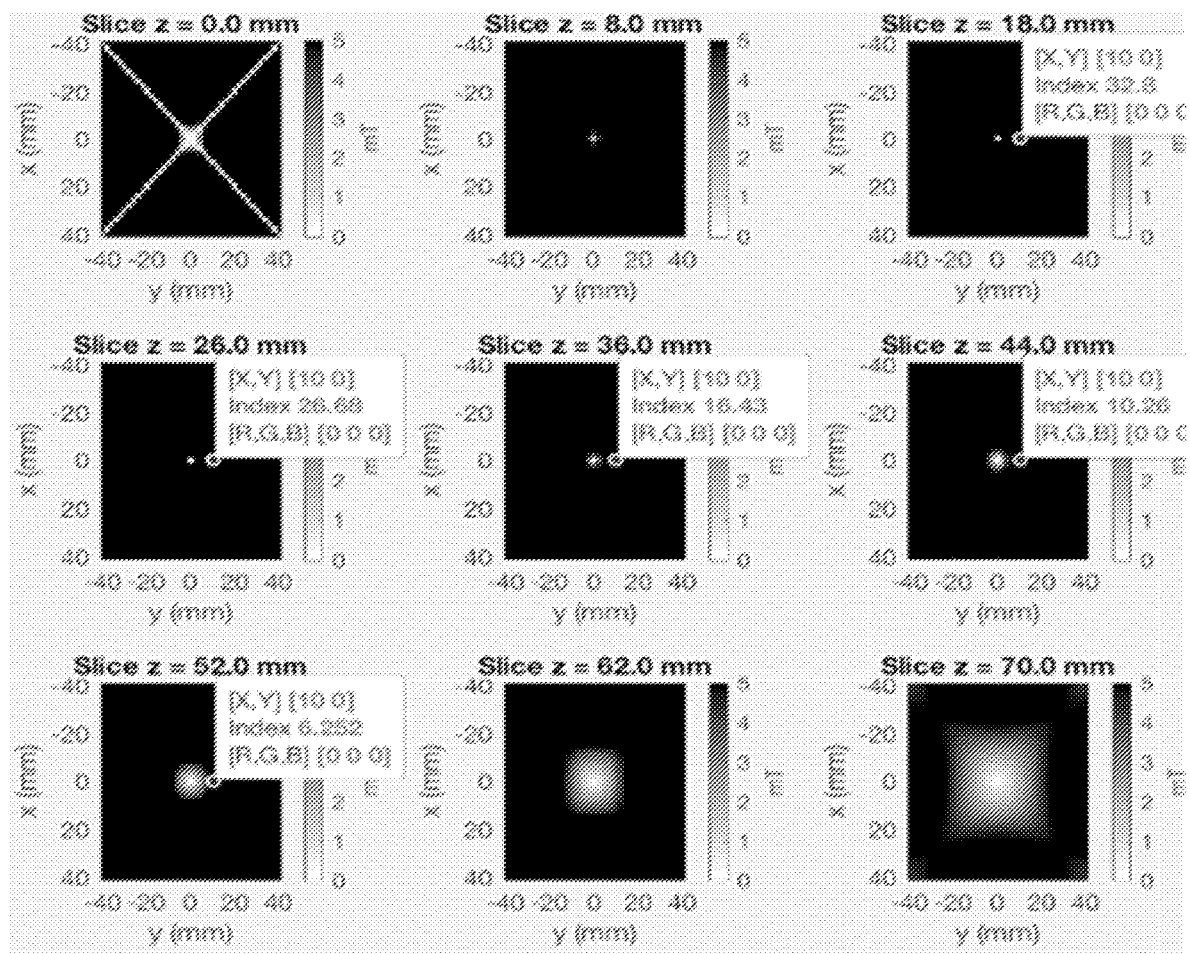
Figure 12.3

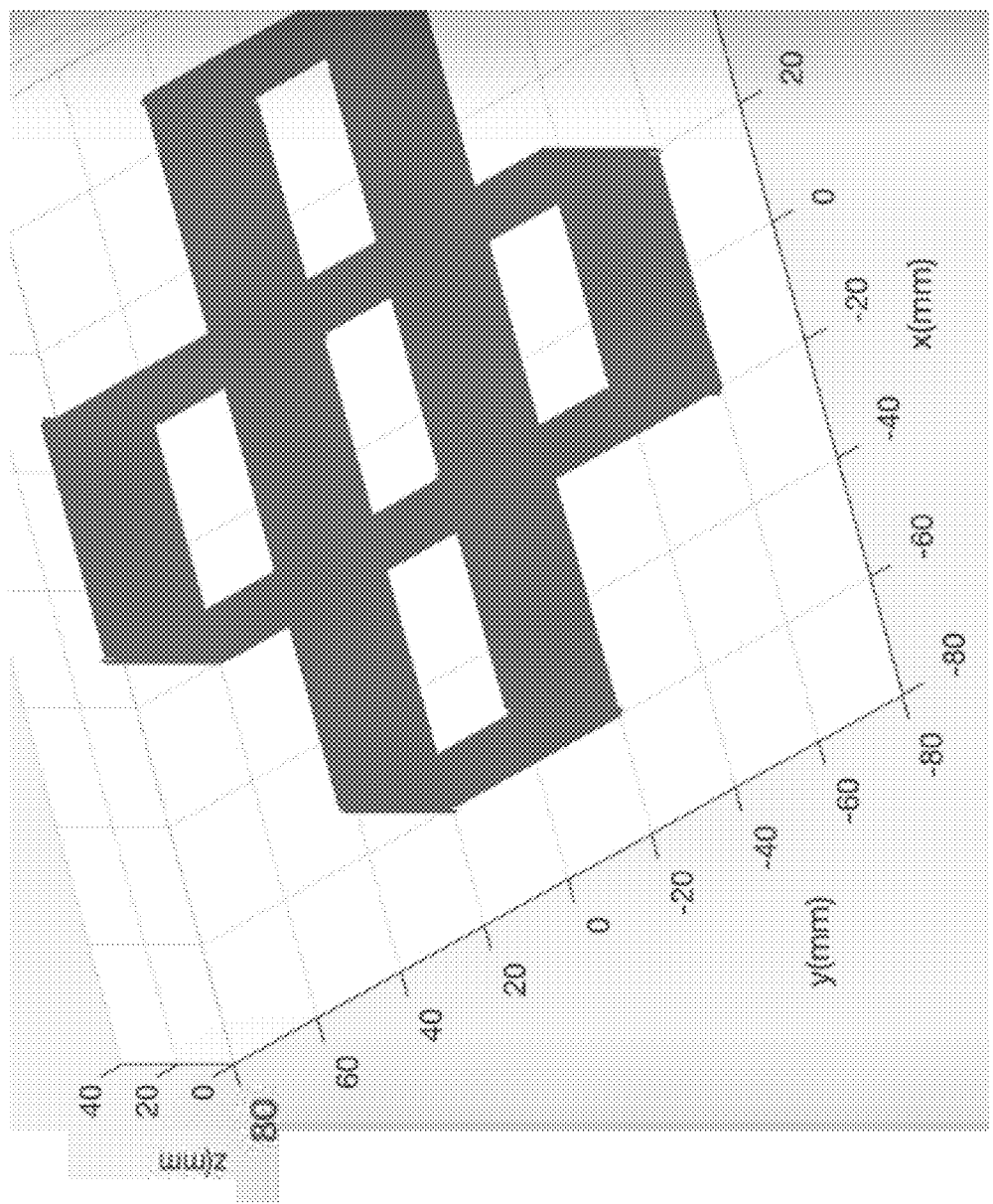
Figure 13.1

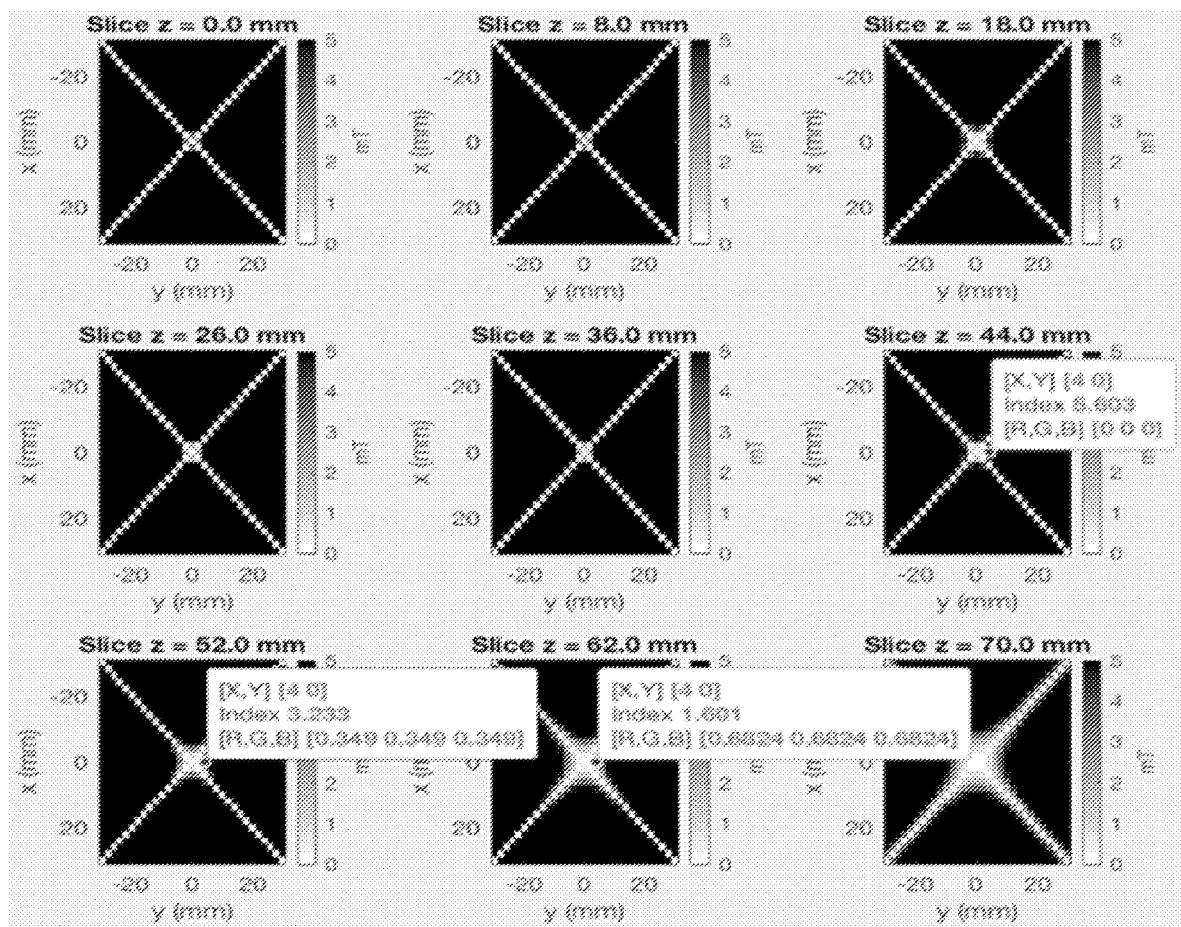
Figure 13.2

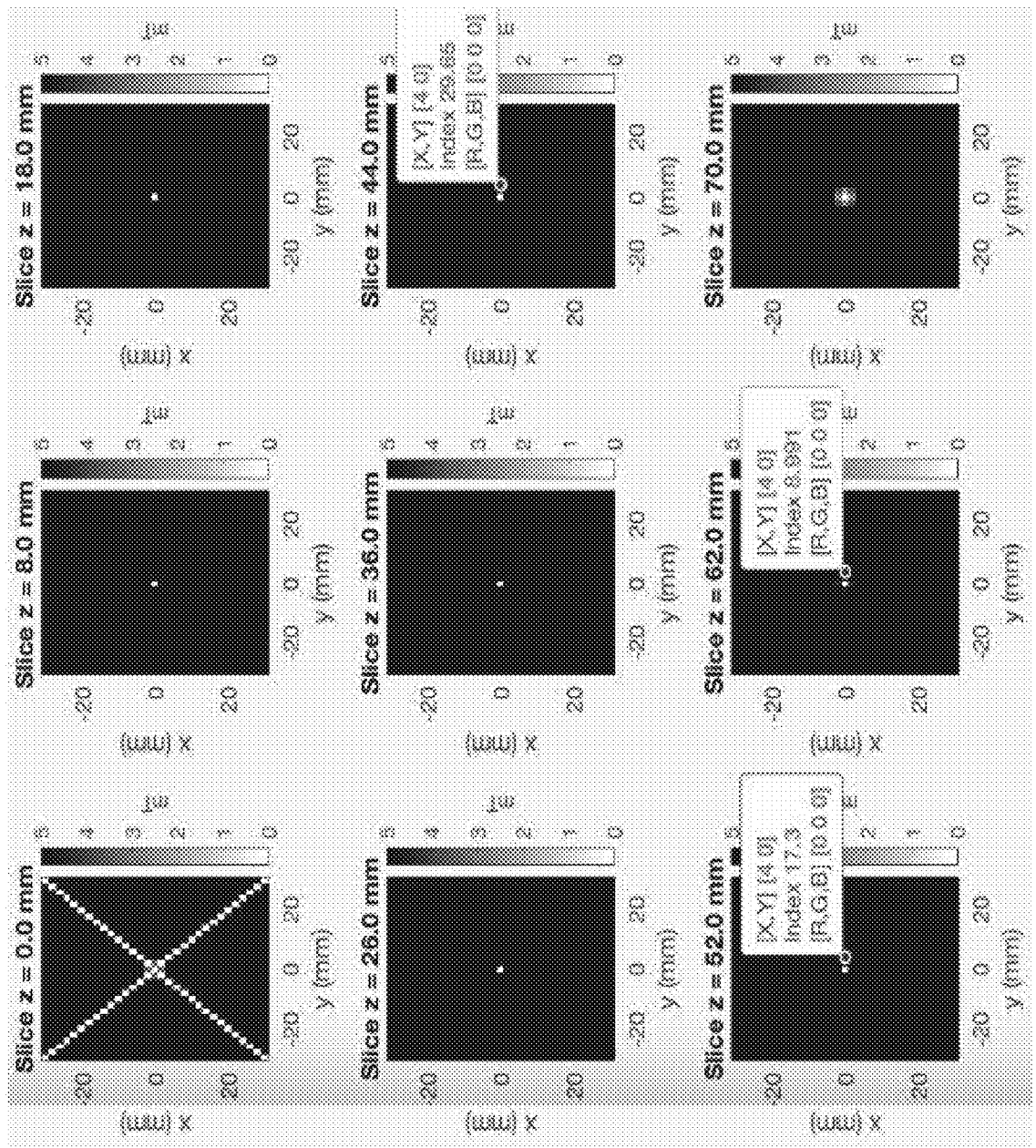
Figure 13.3

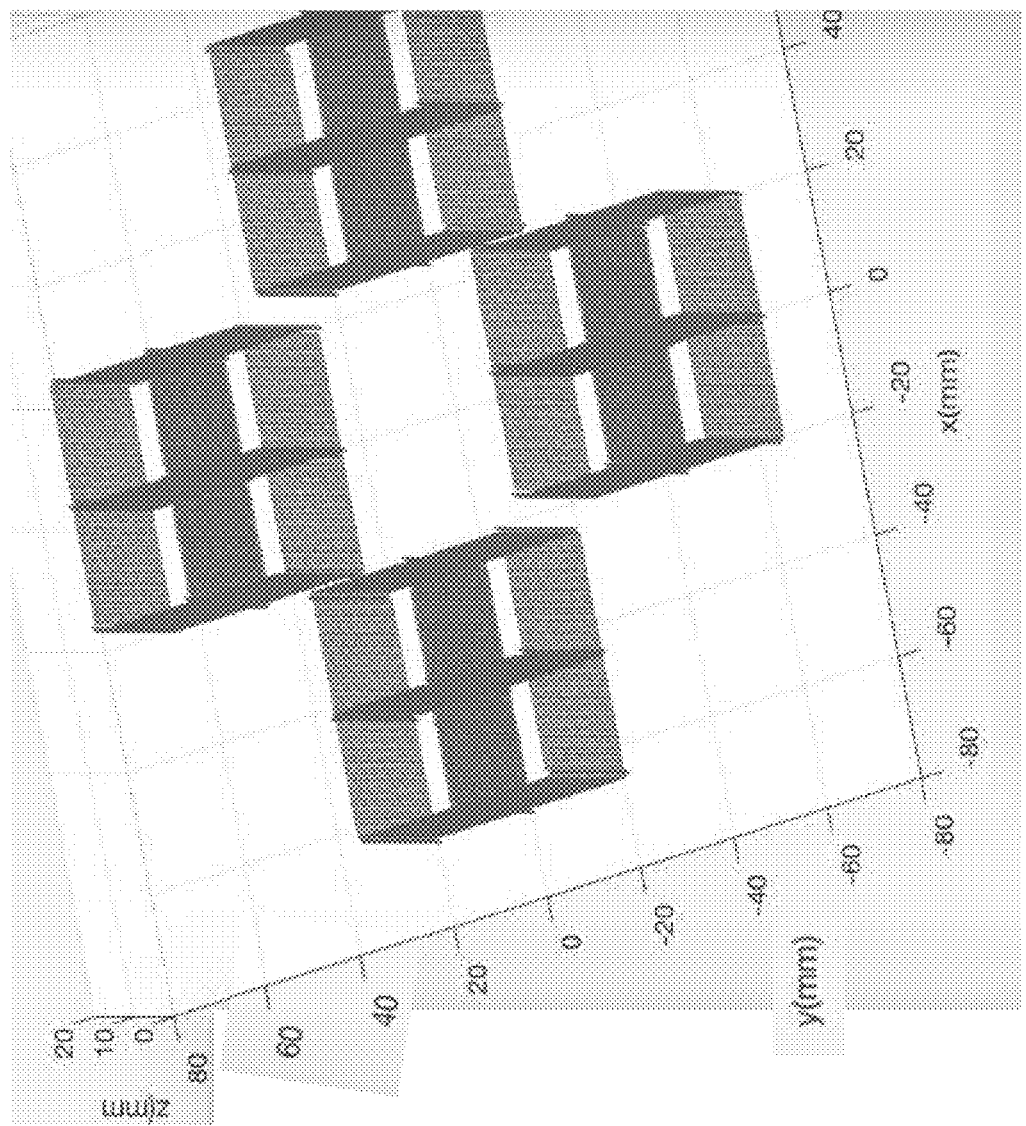
Figure 14.1

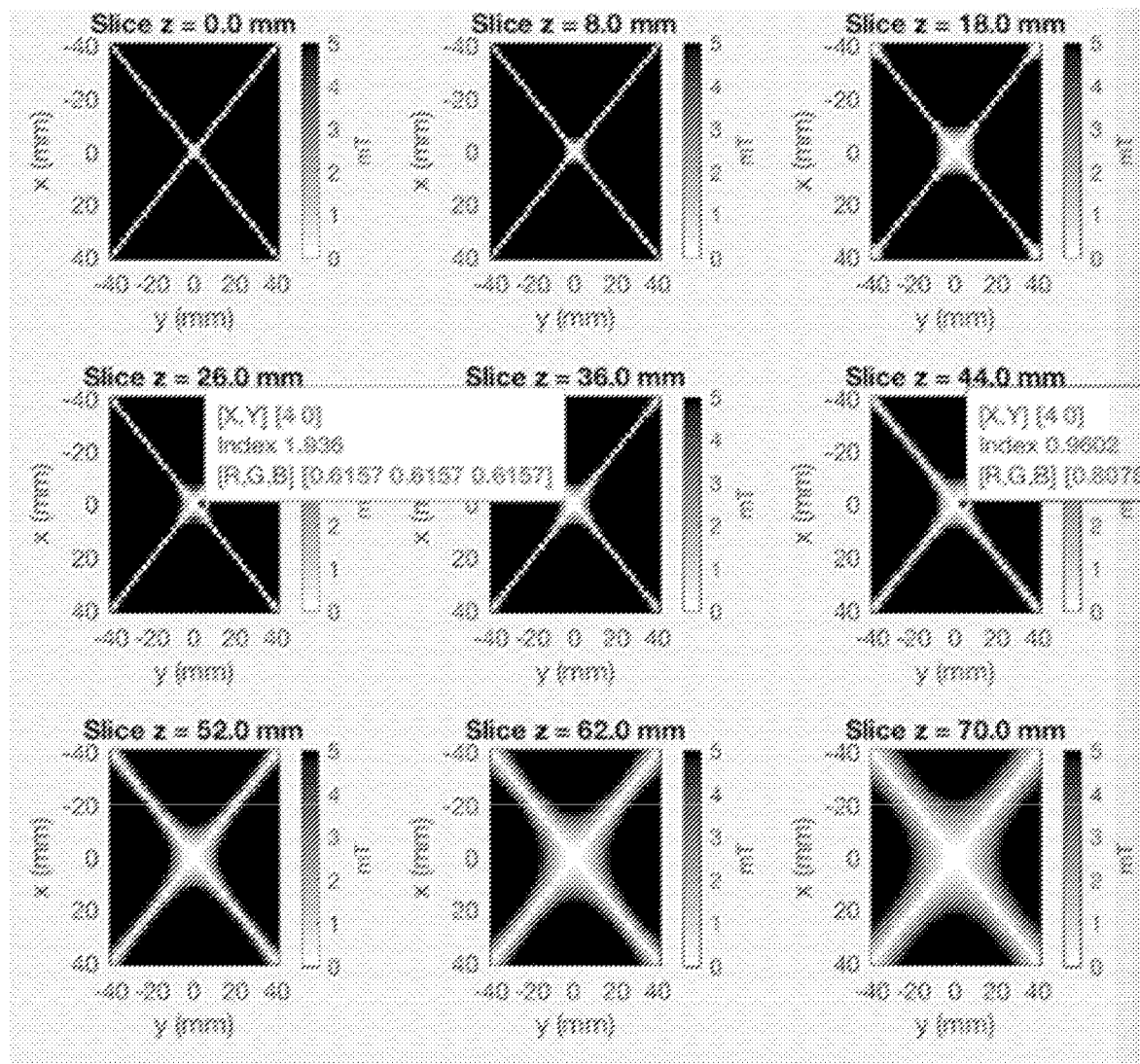
Figure 14.2

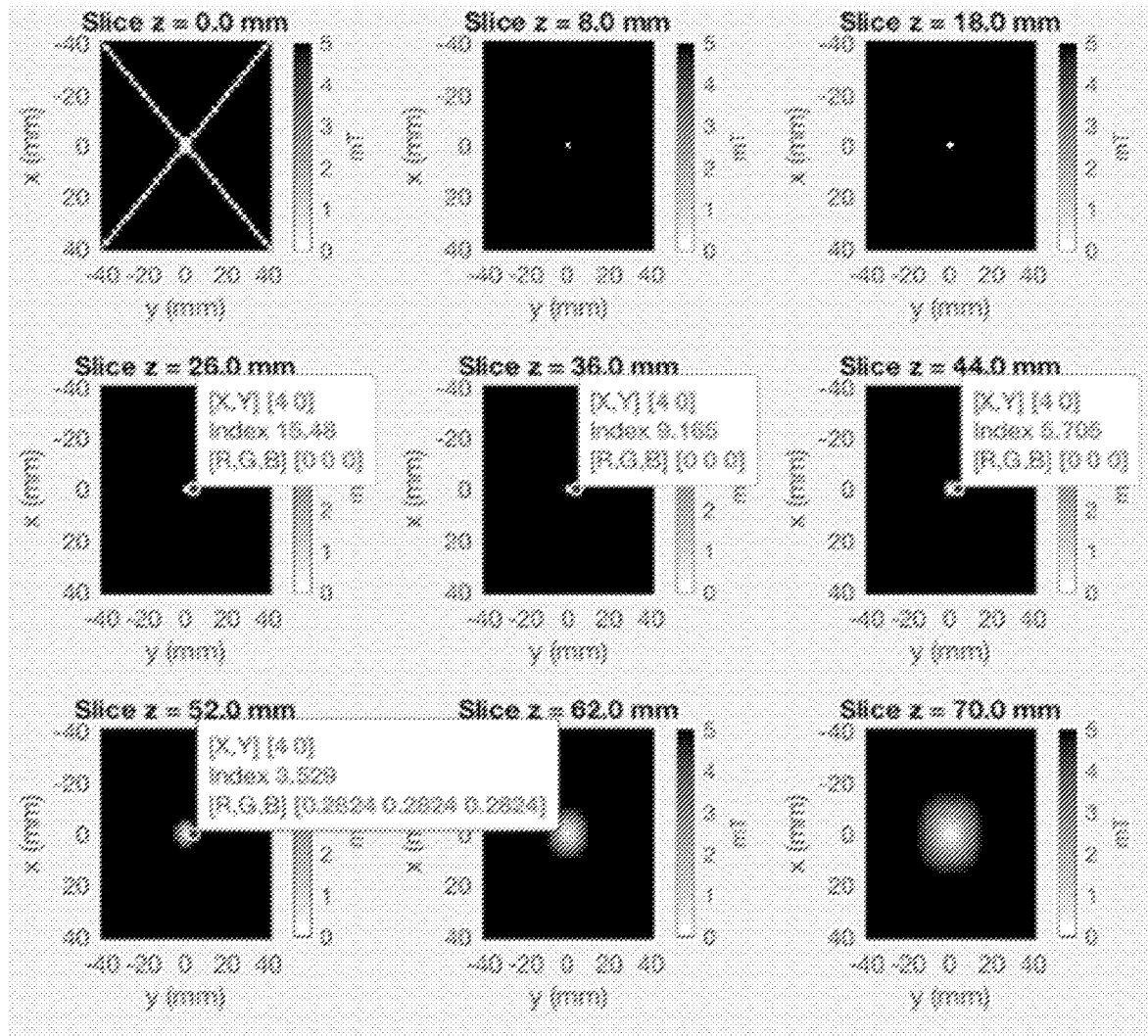
Figure 14.3

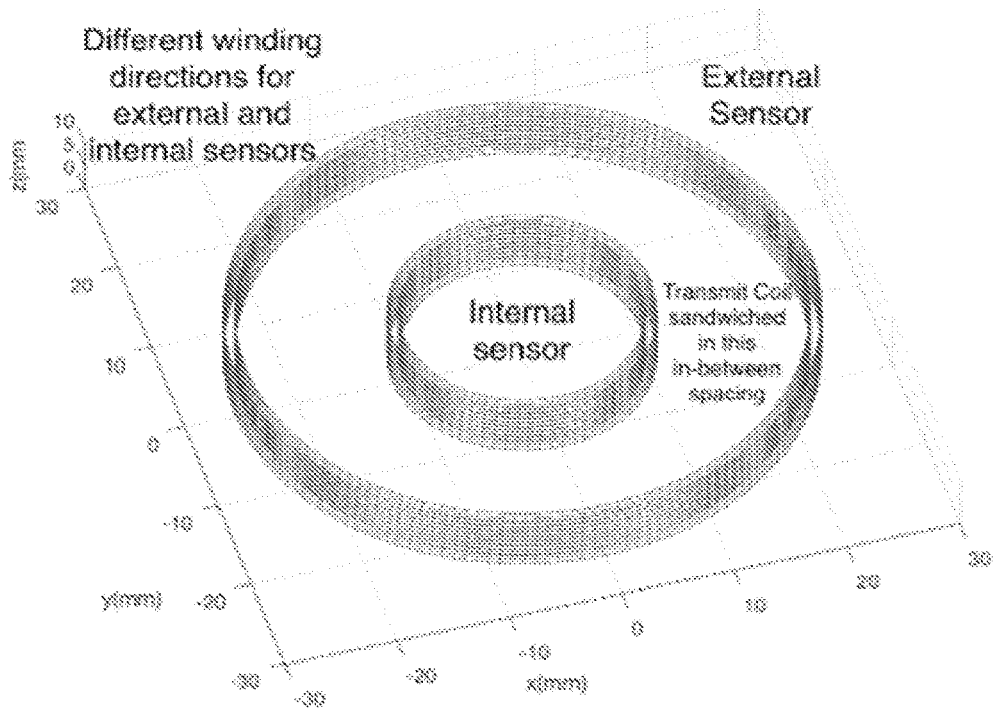
Figure 19.1
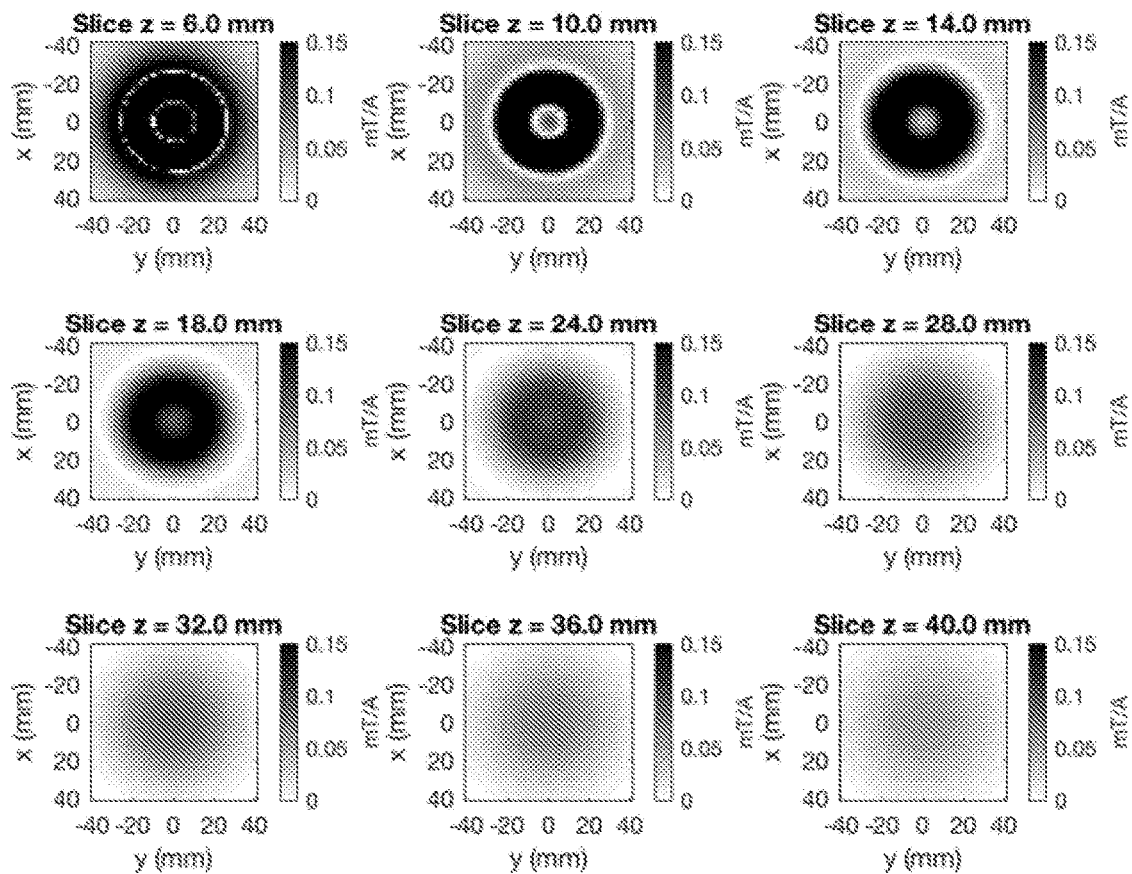
Figure 19.2

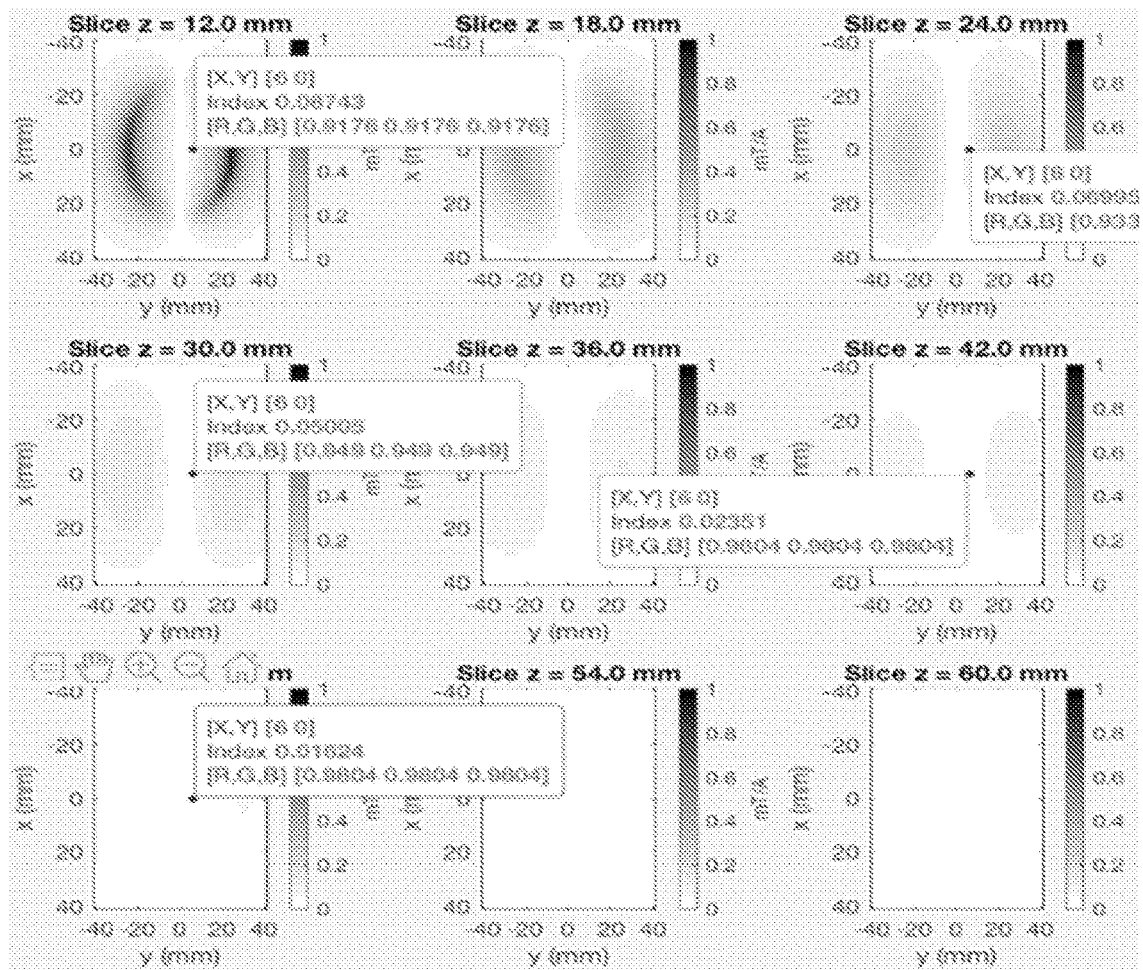
Figure 19.3
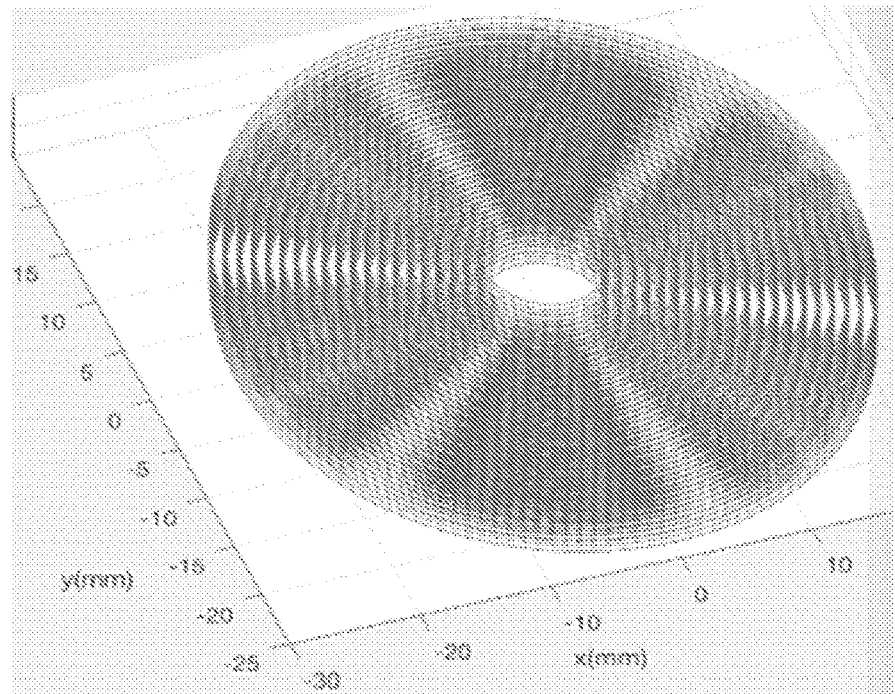
Figure 20.1

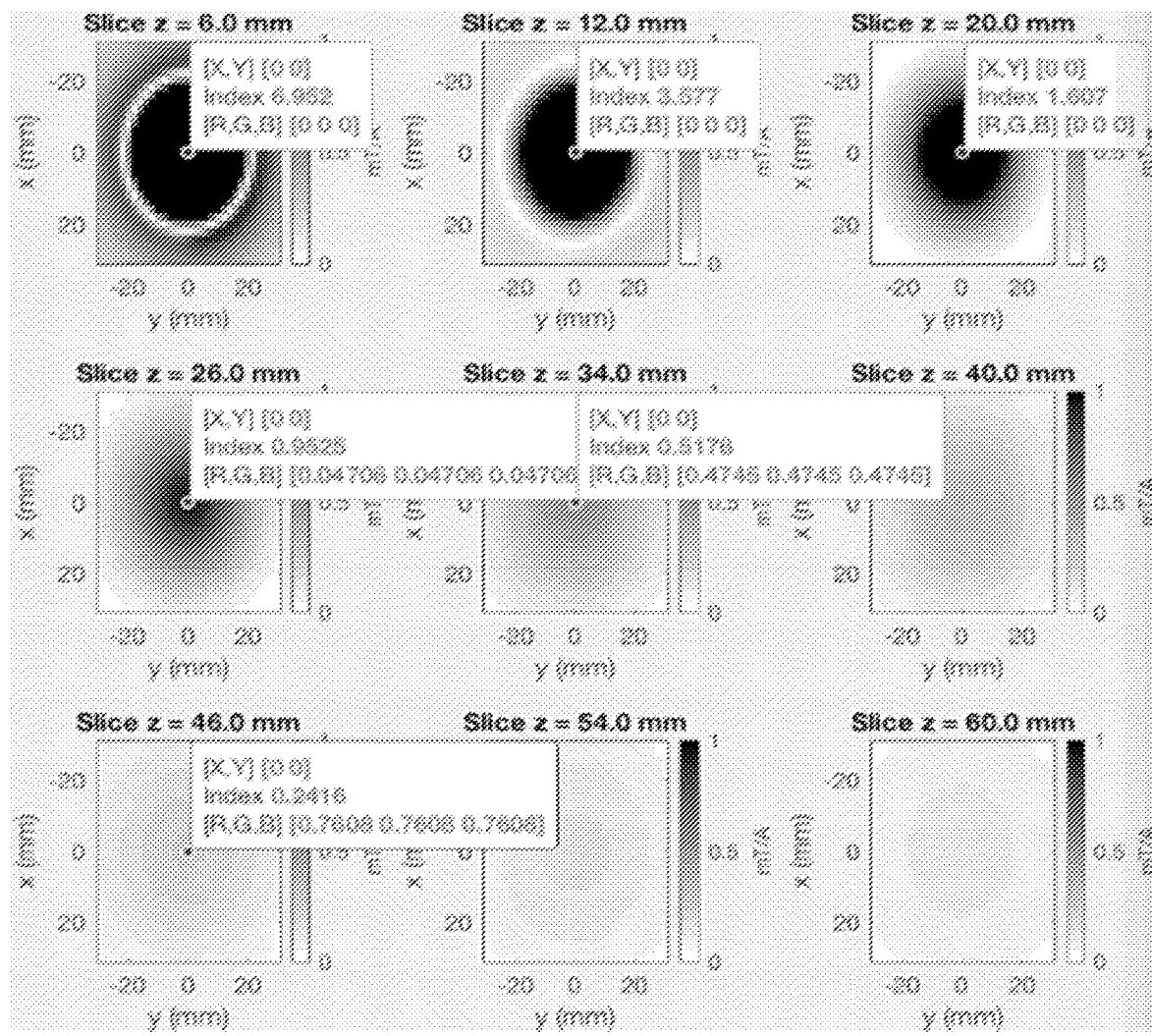
Figure 20.2

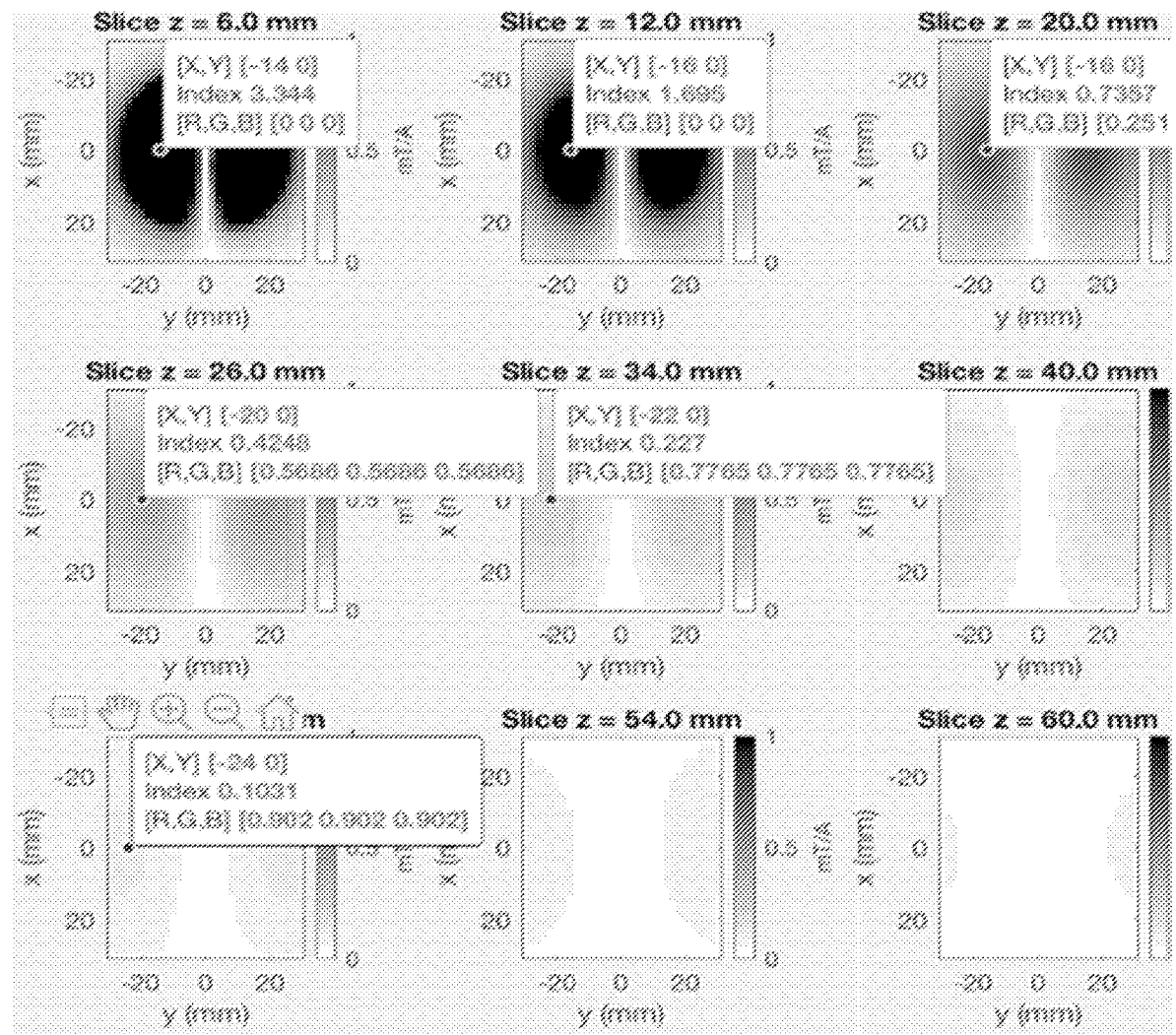
Figure 20.3

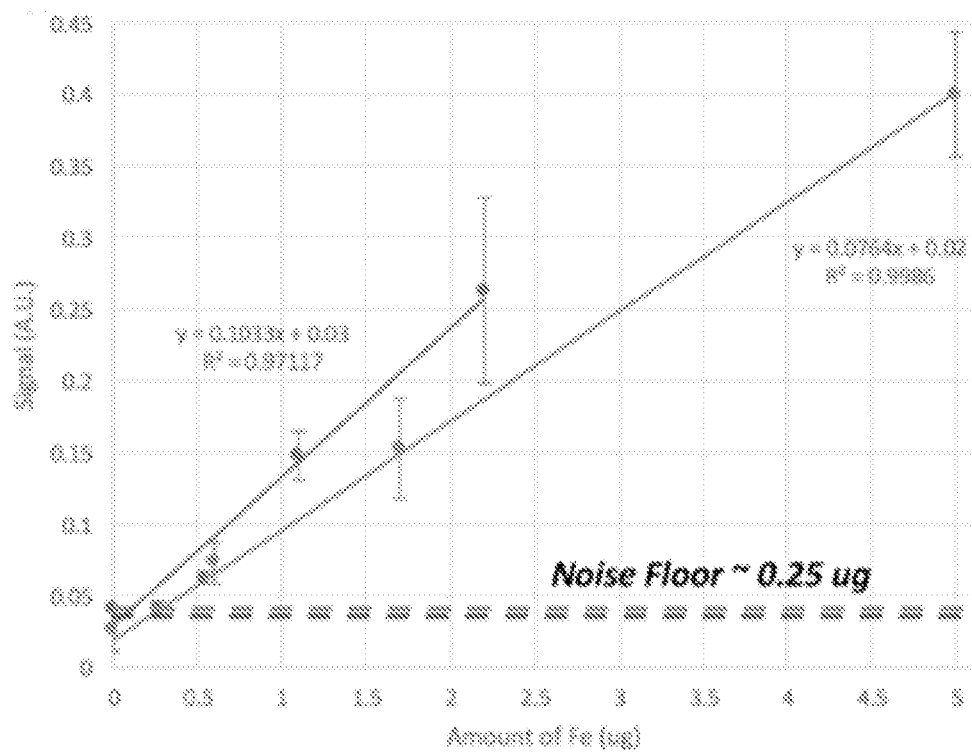
Figure 21
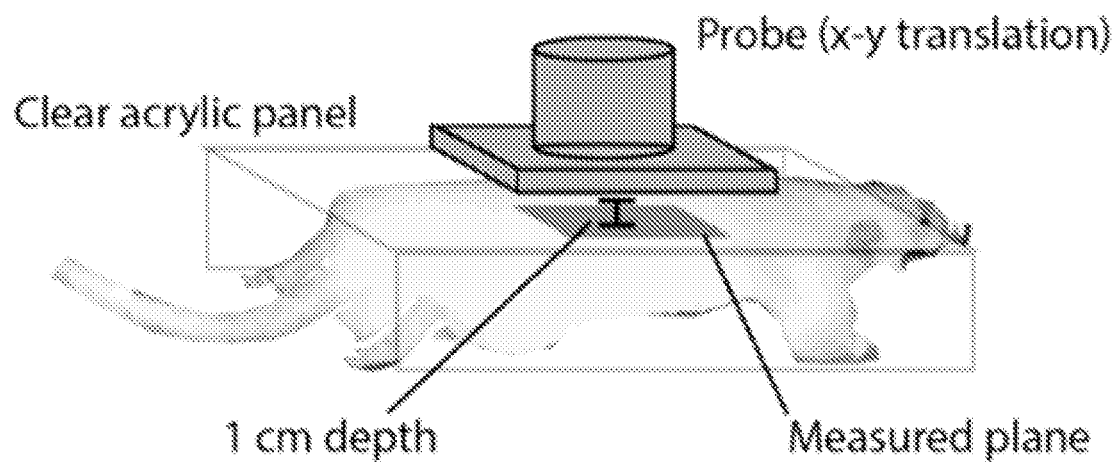
Figure 22.1

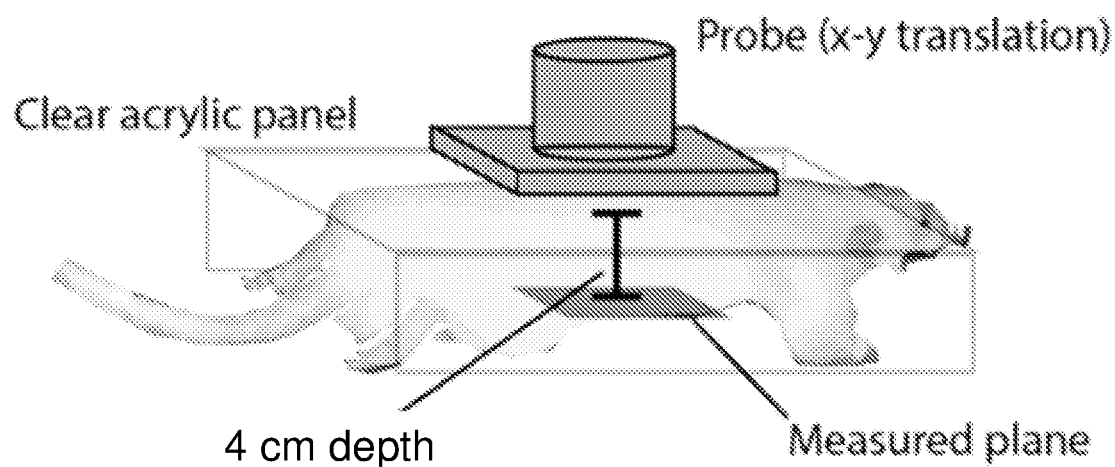
Figure 22.2
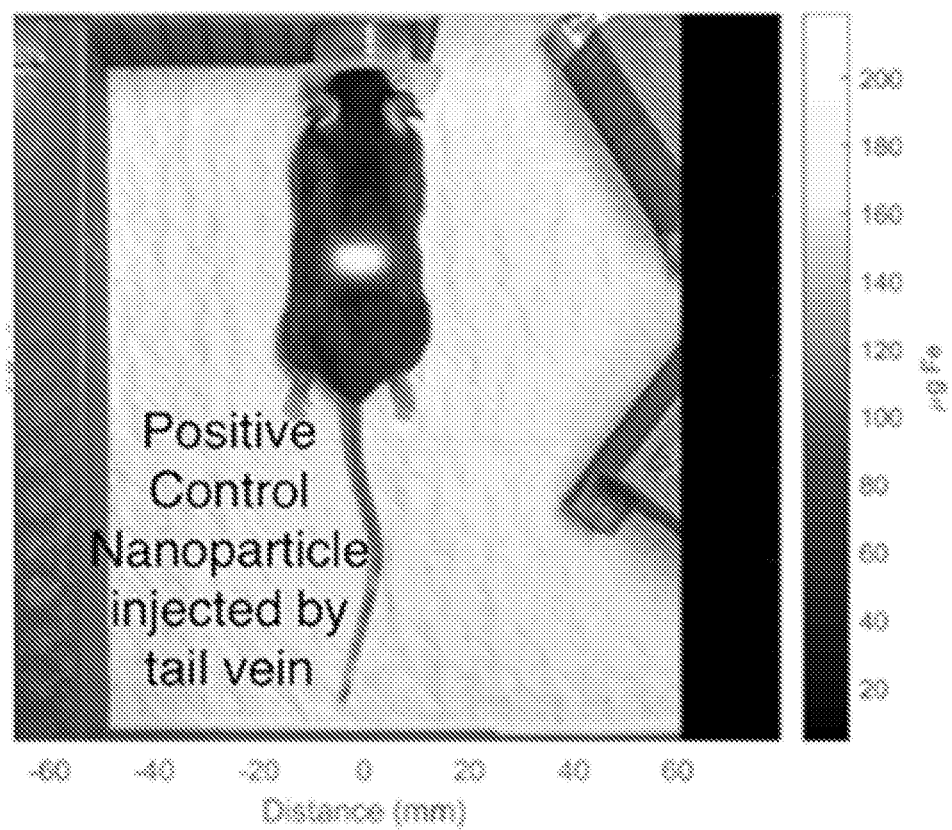
Figure 22.3

PORTABLE HANDHELD MAGNETIC PARTICLE IMAGING

RELATED APPLICATIONS

The subject application is a U.S. National Stage application of International Application No. PCT/SG2021/050424, filed on 19 Jul. 2021, which claims the benefit of Singapore patent Application No. 10202006890P, filed on 20 Jul. 2020. The contents of which are herein incorporated by reference in their entirety.

FIELD OF THE INVENTION

The present disclosure relates to a magnetic particle imaging (MPI) device and method of using the MPI device. The MPI is an imaging modality that detects magnetic nanoparticles contrast agent in a region of interest and constructs images that localize these nanoparticles.

SUMMARY OF THE PRIOR ART

Early-stage detection of cancer is essential for effective treatment but current technologies for cancer screening are limited in their ability to detect early-stage neoplasms. 'Hotspot' tracer imaging techniques such as positron emission tomography (PET) highlight tumors and offer superior image contrast and sensitivity than existing screening techniques (CT, mammogram). However nuclear imaging is not routinely used in the clinic for early cancer screening due to high cost and radioactivity from injected radiotracers.

To circumvent these limitations, a non-invasive and non-radioactive technology to image magnetic nanoparticles (~20 nm) has been introduced. This technology is known as Magnetic Particle Imaging (MPI) and it has already demonstrated 'hotspot' imaging in preclinical rodent models of human cancer. MPI is a tomographic or volumetric imaging technique that detects the magnetization from magnetic particles. However, current MPI systems are still considered expensive and non-portable.

Hence, those skilled in the art are striving to provide a low-cost and portable MPI imaging system with good detection sensitivity of clinical-grade.

SUMMARY OF THE INVENTION

The above and other problems are solved and an advance in the state of the art is made by systems and methods provided by embodiments in accordance with the disclosure. The first advantage of embodiments of systems and methods in accordance with the disclosure is the portability of the system. This allows scanning to take place at any location. Specifically, the handheld design enables more flexibility in imaging as the probe can be lifted and angled to fit a wide range of imaging contexts as compared to relatively immobile and heavy in-bore designs and "moving table single-sided" designs. The second advantage of embodiments of systems and methods in accordance with the disclosure is the cost of producing the system when compared to existing MRI and/or PET/MR scanner. The system is able to provide tracer-like high contrast imaging similar to PET/MR scanner. The third advantage of embodiments of systems and methods in accordance with the disclosure is the adaptability of the handheld probe which can be easily adapted for various uses other than scanning of nanoparticles.

A first aspect of the disclosure relates to a portable magnetic particle imaging (MPI) device. The MPI device comprises a handheld probe comprising a main housing housing a first sensor coil, a second sensor coil, a transmitter coil arranged between the first and second sensor coils, and an excitation priming frame housing magnetic component; and a processing unit comprising a transmitter communicatively connected to the transmitter coil and the excitation priming frame, a receiver communicatively connected to the first and second sensor coils.

In accordance with an embodiment of the first aspect of the disclosure, the excitation priming frame housing is in a shape of a concentric circle and the magnetic components are evenly distributed around the excitation priming frame housing.

In accordance with an embodiment of the first aspect of the disclosure, the excitation priming frame housing is a hexagonal shape and the magnetic components are evenly distributed around the excitation priming frame housing.

In accordance with an embodiment of the first aspect of the disclosure, the magnetic components occupies the excitation priming frame housing.

In accordance with an embodiment of the first aspect of the disclosure, the magnetic components are neodymium magnet.

In accordance with an embodiment of the first aspect of the disclosure, each of the magnetic components is being controlled by the processing unit such that the magnetic components are selectively activated.

In accordance with an embodiment of the first aspect of the disclosure, the first sensor coil and the second sensor coil are two concentric sensor coils with similar winding but different diameter/direction and the transmitter coil concentric is sandwiched between the two concentric sensor coils.

In accordance with an embodiment of the first aspect of the disclosure, the main housing has a convex probe surface.

In accordance with an embodiment of the first aspect of the disclosure, the portable MPI device further comprises an apparatus with a thumb screw adapted for fine translation of one of the first and second sensor coils relative to the transmitter coil.

In accordance with an embodiment of the first aspect of the disclosure, the processing unit further comprises a processor, memory and instructions stored on the memory and executable by the processor to: receive signals from the receiver; and apply spatial encoding to reconstruct the signals to generate a 3 dimensional field-of-view image.

In accordance with an embodiment of the first aspect of the disclosure, the transmitter is configured to generate a fixed known magnetic field in beam shape for the transmitter coil.

In accordance with an embodiment of the first aspect of the disclosure, the transmitter is configured to generate a patterned magnetic field for the priming frame.

In accordance with an embodiment of the first aspect of the disclosure, the portable MPI device further comprises gyroscopic and optical sensors to measure the beam position for image reconstruction.

In accordance with an embodiment of the first aspect of the disclosure, the gyroscopic sensor is arranged a vertical axis of the probe adapted to sense tilt when the probe is conically tilted to interrogate a conic field-of-view.

In accordance with an embodiment of the first aspect of the disclosure, the gyroscopic sensor is arranged at two points along a perimeter of the priming frame.

In accordance with an embodiment of the first aspect of the disclosure, the portable MPI device further comprises an ultrasound control and receiver adapted to provide an anatomic reference.

In accordance with an embodiment of the first aspect of the disclosure, the ultrasound control and receiver is adjacently coupled to the handheld probe.

In accordance with an embodiment of the first aspect of the disclosure, the portable MPI further comprises a mountable adapter for receiving the handheld probe.

BRIEF DESCRIPTION OF THE DRAWINGS

The above advantages and features in accordance with this invention are described in the following detailed description and are shown in the following drawings:

FIG. 1.1 illustrates an overall schematic of the hardware of the hMPI system in accordance with an embodiment of this invention;

FIG. 1.2 illustrates a MPI measured M-H curve of nanoparticles at different depths away from the probe sensor surface;

FIG. 1.3 illustrates a MPI measured harmonic spectra of nanoparticles at different depths away from the probe sensor surface;

FIG. 6 illustrates another embodiment of a priming frame of the handheld probe of the hMPI system in accordance with an embodiment of this invention;

FIG. 7.1 illustrates a first arrangement of the magnetic component in the priming frame of the handheld probe of the hMPI system in accordance with an embodiment of this invention;

FIG. 7.2 illustrates the z-direction magnetic field of the first arrangement taken at nine slices as shown in FIG. 7.1;

FIG. 7.3 illustrates the net magnitude of magnetic field of the first arrangement taken at nine slices by Gaussmeter-calibrated mapping as shown in FIG. 7.1;

FIG. 8.1 illustrates a second arrangement of the magnetic component in the priming frame of the handheld probe of the hMPI system in accordance with an embodiment of this invention;

FIG. 8.2 illustrates the z-direction magnetic field of the second arrangement taken at nine slices as shown in FIG. 8.1;

FIG. 8.3 illustrates the net magnitude of magnetic field of the second arrangement taken at nine slices by Gaussmeter-calibrated mapping as shown in FIG. 8.1;

FIG. 9.1 illustrates a third arrangement of the magnetic component in the priming frame of the handheld probe of the hMPI system in accordance with an embodiment of this invention;

FIG. 9.2 illustrates the z-direction magnetic field of the third arrangement taken at nine slices as shown in FIG. 9.1;

FIG. 9.3 illustrates the net magnitude of magnetic field of the third arrangement taken at nine slices by Gaussmeter-calibrated mapping as shown in FIG. 9.1;

FIG. 10.1 illustrates a fourth arrangement of the magnetic component in the priming frame of the handheld probe of the hMPI system in accordance with an embodiment of this invention;

FIG. 10.2 illustrates the z-direction magnetic field of the fourth arrangement taken at nine slices as shown in FIG. 10.1;

FIG. 10.3 illustrates the x-direction magnetic field of the fourth arrangement taken at nine slices by Gaussmeter-calibrated mapping as shown in FIG. 10.1;

FIG. 11.1 illustrates a fifth arrangement of the magnetic component in the priming frame of the handheld probe of the hMPI system in accordance with an embodiment of this invention;

FIG. 11.2 illustrates the z-direction magnetic field of the fifth arrangement taken at nine slices as shown in FIG. 11.1;

FIG. 11.3 illustrates the x-direction magnetic field of the fifth arrangement taken at nine slices by Gaussmeter-calibrated mapping as shown in FIG. 11.1;

FIG. 12.1 illustrates a sixth arrangement of the magnetic component in the priming frame of the handheld probe of the hMPI system in accordance with an embodiment of this invention;

FIG. 12.2 illustrates the z-direction magnetic field of the sixth arrangement taken at nine slices as shown in FIG. 12.1;

FIG. 12.3 illustrates the net magnitude of magnetic field of the sixth arrangement taken at nine slices by Gaussmeter-calibrated mapping as shown in FIG. 12.1;

FIG. 13.1 illustrates a seventh arrangement of the magnetic component in the priming frame of the handheld probe of the hMPI system in accordance with an embodiment of this invention;

FIG. 13.2 illustrates the z-direction magnetic field of the seventh arrangement taken at nine slices as shown in FIG. 13.1;

FIG. 13.3 illustrates the net magnitude of magnetic field of the seventh arrangement taken at nine slices by Gaussmeter-calibrated mapping as shown in FIG. 13.1;

FIG. 14.1 illustrates an eight arrangement of the magnetic component in the priming frame of the handheld probe of the hMPI system in accordance with an embodiment of this invention;

FIG. 14.2 illustrates the z-direction magnetic field of the eight arrangement taken at nine slices as shown in FIG. 14.1;

FIG. 14.3 illustrates the net magnitude of magnetic field of the eight arrangement taken at nine slices by Gaussmeter-calibrated mapping as shown in FIG. 14.1;

FIG. 19.1 illustrates an arrangement of the outside and inside sensor coil relative to the transmit coil of the handheld probe of the hMPI system in accordance with an embodiment of this invention;

FIG. 19.2 illustrates the z-direction magnetic field (sensitivity map) of the arrangement of the sensor coil as shown in FIG. 19.1 taken at nine slices.

FIG. 19.3 illustrates the x-direction magnetic field of the arrangement of the transmit coil as shown in FIG. 19.1 taken at nine slices;

FIG. 20.1 illustrates an arrangement of the transmit coil of the handheld probe of the hMPI system in accordance with an embodiment of this invention;

FIG. 20.2 illustrates the z-direction magnetic field of the arrangement of the transmit coil as shown in FIG. 20.1 taken at nine slices;

FIG. 20.3 illustrates the x-direction magnetic field of the arrangement of the transmit coil as shown in FIG. 20.1 taken at nine slices;

FIG. 21 illustrates the sensitivity of the hMPI system in accordance with this invention being benchmarked against Prussian Blue Histology standard;

FIGS. 22.1 and 22.2 illustrate a preclinical imaging setup for using the hMPI system in accordance with this invention;

FIG. 22.3 illustrates an image of a rodent with positive control nanoparticle injected by tail vein;

DETAILED DESCRIPTION

Figure 2:
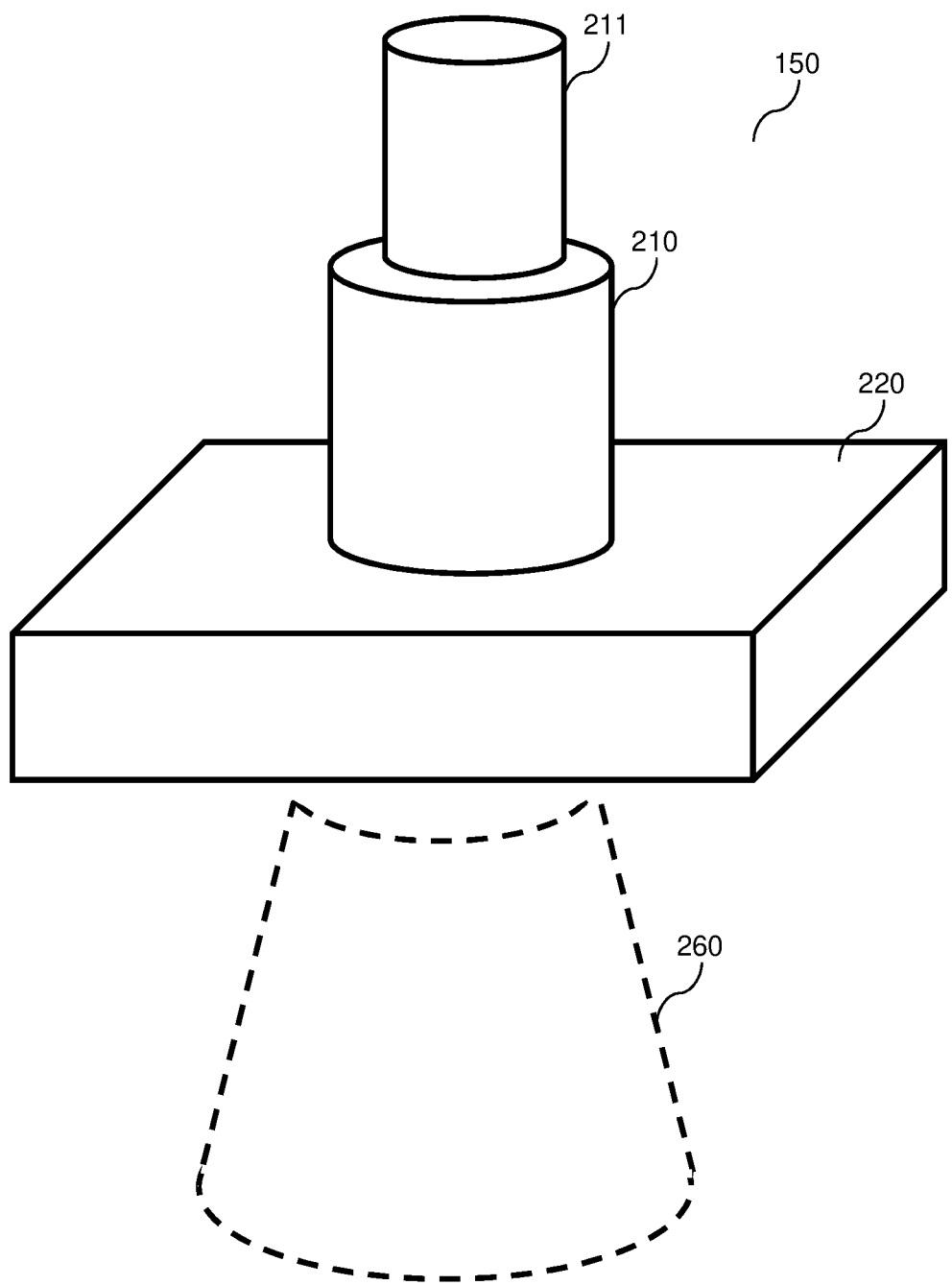
FIG. 2 illustrates a perspective view of a handheld probe of the hMPI system in accordance with an embodiment of this invention.

The present disclosure relates to a magnetic particle imaging (MPI) device and method of using the MPI device. The MPI is an imaging modality that detects magnetic nanoparticles contrast agent in a region of interest and constructs images that localize these nanoparticles.

Magnetic Particle Imaging (MPI) is an imaging modality that detects magnetic nanoparticles contrast agent in a region of interest and constructs images that localize these nanoparticles. This disclosure discloses a portable, handheld magnetic particle imaging (hMPI) system according to an embodiment of the invention. The hMPI system in accordance with this invention is 10 times cheaper to manufacture and occupies less than a-third footprint of existing MPI systems. Trial results of the hMPI system have shown good detection sensitivity of clinical-grade and functionalized magnetic nanoparticles.

The hMPI system in accordance with this invention distinguishes itself from existing MPI imaging technology through new acquisition, scanning and reconstruction strategies that enable portable MPI using a small handheld probe as opposed to larger non-portable scanners in existing MPI where the imaging device itself is very bulky and support equipment is in external server racks across the room from the device.

The hMPI system in accordance with this invention generates a spatially patterned static magnetic field with a spatial distribution of magnetic field strength and direction.

FIG. 1.1 illustrates a hMPI system 100 in accordance with an embodiment of this invention. The hMPI system 100 includes a processing unit 110, a thermal cooling unit 120, a transmitter 130, a receiver 140 and a handheld probe 150. In some embodiment, the hMPI system 100 further includes an ultrasound control and receiver 160.

The processing unit 110 is a typical computing system that comprises a processor, memory and instructions stored on the memory and executable by the processor. The processor may be a processor, microprocessor, microcontroller, application specific integrated circuit, digital signal processor (DSP), programmable logic circuit, or other data processing device that executes instructions to perform the processes in accordance with the present invention. The processor has the capability to execute various applications that are stored in the memory. The memory may include read-only memory (ROM), random-access memory (RAM), electrically erasable programmable ROM (EEPROM), flash cards, or any storage medium. Instructions are computing codes, software applications that are stored on the memory and executable by the processor to perform the processes in accordance with this invention. Such computing system is well known in the art and hence only briefly described herein. The instructions can developed in Python, Java or C++ language (or any other known programming language) and can be run on System on Chip (SoC) like Raspberry Pi and/or mobile devices like cell phones or tablet PCs and/or desktop PCs.

A set of instructions may be provided on the memory and executable by the processor for image reconstruction which will be performed with the signals received from the sensor coils on the gyroscopic and optical translation sensors in the handheld probe 150 to provide the 3D position and direction vector/tilt of the "magnetic beam". Acquired signals from the sensor coils correspond temporally to the instantaneous 3D position and direction of the beam will be assigned to that spatial beam position and direction. Spatial encoding within the beam itself is performed by the difference in magnetic field strength drop-off with distance for the static field and the excitation system, resulting in excitation of the nanoparticles along different sub-sections of the magnetic nanoparticle magnetization response curve (M-H) curve depending on the distance along the beam axis from the hMPI probe. For example, nanoparticles closer to the hMPI probe traverse the M-H curve to a further extent in H-field from the zero-crossing point, generating a different magnetization signature from nanoparticles farther from the hMPI probe that traverses the M-H curve closely around both sides of the zero-crossing point due to a shorter extent of the H-field. FIG. 1.1 shows a MPI measured M-H curve of nanoparticles at different depths away from the probe sensor surface. Clear differences in the curve shape are observed after normalizing to peak height. These differences can be resolved by de-convolution or other inverse problem algorithms to assign the signal within the beam-axis to different depth locations along the beam. FIG. 1.3 shows a MPI measured harmonic spectra of nanoparticles at different depths away from the probe sensor surface. Clear differences in spectra slope are observed after normalizing to f0 height. These differences can be resolved by de-convolution or other inverse problem algorithms to assign the signal within the beam-axis to different depth locations along the beam. Furthermore, the use of internal and external pair of sensors sandwiching the transmitter coil leads to a sensitivity map that will invert the nanoparticle signal in a depth-dependent manner along the central magnetic beam (see FIG. 19.2), and thus will greatly help in spatial encoding within the beam axis when used in conjunction with abovementioned spatial encoding strategies.

A set of instructions may be provided on the memory and executable by the processor for image reconstruction may also include instructions for reconstructing multiple smaller field-of-view. Larger field-of-view or whole-body images can be reconstructed from multiple smaller field-of-view with knowledge of the 3D position of the hMPI probe via translation sensors. The overlapping images of smaller fieldof-views can be stitched together in reconstruction in the same fashion as camera panorama image algorithms.

A set of instructions may be provided on the memory and executable by the processor for monitoring the position of the handheld probe 150 and will prompt the operator to cover all angles of tilt to fully sweep the "magnetic beam" across entire 3D conic volume, obviating the need for strong electromagnets to shift the generated magnetic field around.

The acquisition trajectory of tilting a "beam" through a 3D conic volume is distinguishing from existing MPI using a raster trajectory or a Lissajous trajectory for the field-free-point or field-freeline, and is also distinguished from the 2D conic sections of ultrasound with finite slice thickness.

A set of instructions may be provided on the memory and executable by the processor for triggering monotonous (sinusoidal) or arbitrary function excitation pulse sequence for the hMPI excitation to enable different methods of spatial encoding.

The recorded sensor data on the gyroscopic and optical translation sensors will also provide the 3D position and direction vector/slice thickness of the ultrasound to reconstruct a 3D ultrasound conic volume section for anatomic reference to co-register the hMPI 3D conic volume section.

The thermal cooling unit 120 is essentially a heat sink with a fan arranged above the transmitter and receiver coils in the handheld probe to cool the transmitter and receiver coils. Further details on the arrangement of the thermal cooling unit 120 would be described below with reference to FIGS. 2 and 3.

The transmitter 130 is a generation system for a generating a magnetic field. The generation system includes at least one magnet, where the magnetic field within the observation region is spatially structured without a field free region (FFR) for an object under observation to 'prime' the magnetic nanoparticles, but where the directional excitation system can interact with the patterned magnetic field to generate spatial patterns of spatial selective excitation of magnetic nanoparticles. Before using the hMPI system 100 on a subject (or patient), the subject would be injected with substance containing magnetic nanoparticle tracer detectable by the MPI system.

The transmitter 130 comprises an MPI power amplifier 131 and transmit filters 132. The transmitter 130 further comprises an excitation system 133 for providing signals to the priming frame. The MPI power amplifier 131 amplifies signal generated by the processing unit 110. Specifically, the processing unit generates a signal to be amplified by the power amplifier 131. This signal will be coordinated with other signals to the priming frame for the case of electromagnets or movable magnets on the priming frame serving as signal enhancer or dampener purpose with a spatial pattern. Preferably, the MPI power amplifier should provide 1100-2200 W of power across 0.1 kHz-100 kHz to accommodate a wide range of MPI scan strategies. The transmit filters 132 are provided to generate signal at a required frequency. This signal at the required frequency is transmitted to the transmitter coil in the handheld probe 150. The transmit filters improve the fidelity of the transmitter coil signal but are not always required.

Essentially, the transmitter is configured to generate two signals, a fixed known magnetic field in beam shape and patterned magnetic fields. The fixed known magnetic field in beam shape is for the transmit coil 1730 serving as an excitation purpose to elicit response from magnetic nanoparticles. The patterned magnetic fields is for the priming frame serving as signal enhancer or dampener purpose with a spatial pattern. In this embodiment, the electromagnets are used in the priming frame and the transmit coil 1730. In another embodiment where permanent magnets are used in the priming frame, the transmitter does not need to signal the priming frame.

The receiver 140 comprises a MPI receiver filter 141 to receive the signal at a desired frequency from the receiver coil in the handheld probe 150. The received signal is then transmitted to the MPI preamplifier to amplify the received signal before being translated from analogue to digital signal by the analogue to digital converter (ADC) 143. The digital signal is then transmitted to the processing unit 110 which will in turn process the digital signal. The ADC 143 may also be used for filtering (high-pass or band-stop) of the excitation frequency to further improve direct feedthrough mitigation to better than 100 dB.

The ultrasound control and receiver 160 may be added. The hMPI system 100 may be integrated with the ultrasound control and receiver 160 to provide the anatomic reference as opposed to MPI integrated with CT or MRI due to the similar of the "in-bore" imaging context. In other words, the hMPI system 100 is capable of simultaneously acquiring both the ultrasound anatomic reference and MPI image.

To minimize cross-talk between the electronic circuits of hMPI and ultrasound, the hMPI operating frequency range will be between 10 Hz-1 MHz, while the ultrasound operating frequency range will be above 1 MHz.

The recorded sensor data on the gyroscopic and optical translation sensors will also provide the 3D position and direction vector/slice thickness of the ultrasound to reconstruct a 3D ultrasound conic volume section for anatomic reference to co-register the hMPI 3D conic volume section.

Figure 3:
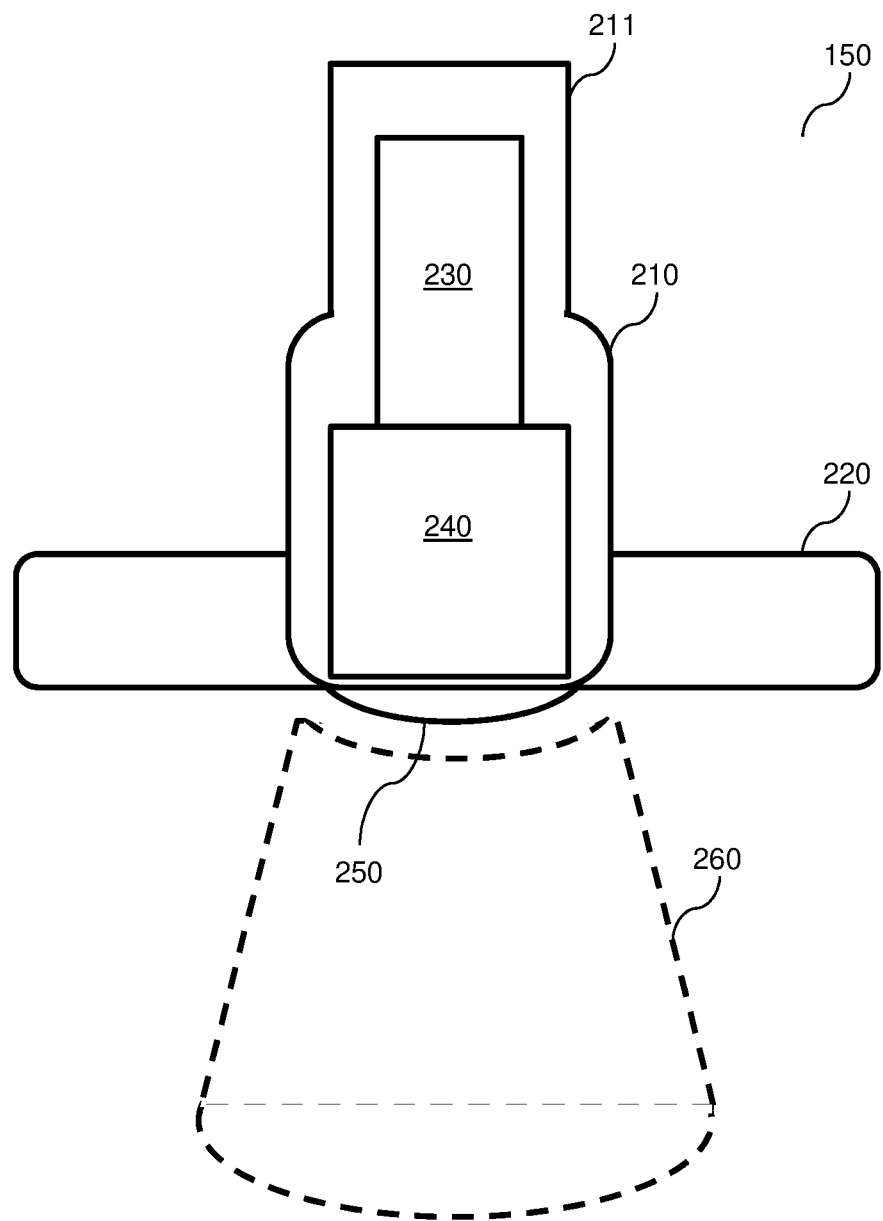
FIG. 3 illustrates a cross sectional view of the handheld probe of the hMPI system in accordance with an embodiment of this invention.

FIG. 2 shows a perspective view of the handheld probe 150. FIG. 3 shows a cross sectional view of the handheld probe 150. The handheld probe 150 includes a housing 210 with an ergonomic handheld grip 211; a thermal cooling section 230 that is communicatively connected to the thermal cooling unit 120; an MPI transmitter and receiver compartment 240 housing a transmitter that is communicatively connected to the MPI power amplifier 131 or the transmit filters 132 and a receiver that is communicatively connected to the receiver 140; and a MPI priming frame 220 that is communicatively connected to the excitation system 133.

One key distinguishing feature of the hMPI system 100 is there does not exist a sub-area with low or null magnetic field strength and although the generated magnetic field is spatially inhomogeneous, there is sufficient magnetic field strength everywhere to 'prime' all nanoparticles in the field-of-view to reach the nonlinear magnetization response of magnetic nanoparticles. This is achieved by the arrangement of the magnetic components in the MPI priming frame 220. The magnetic components is arranged proximate to the observation region to create an excitation region. This excitation region has a magnetic field direction and magnetic field strength spatial drop-off designed to interact with the static field to produce spatial patterns of excitation in the nanoparticle distribution within the observation region. The magnetic components in the MPI priming frame 220, either permanent magnet or electromagnet, are spatially arrayed to produce the required magnetic field spatial shape in 3D for hMPI. The components can either be passive, or actively controlled by the processing unit i.e. electromagnet, shiftable parts.

Figure 4:
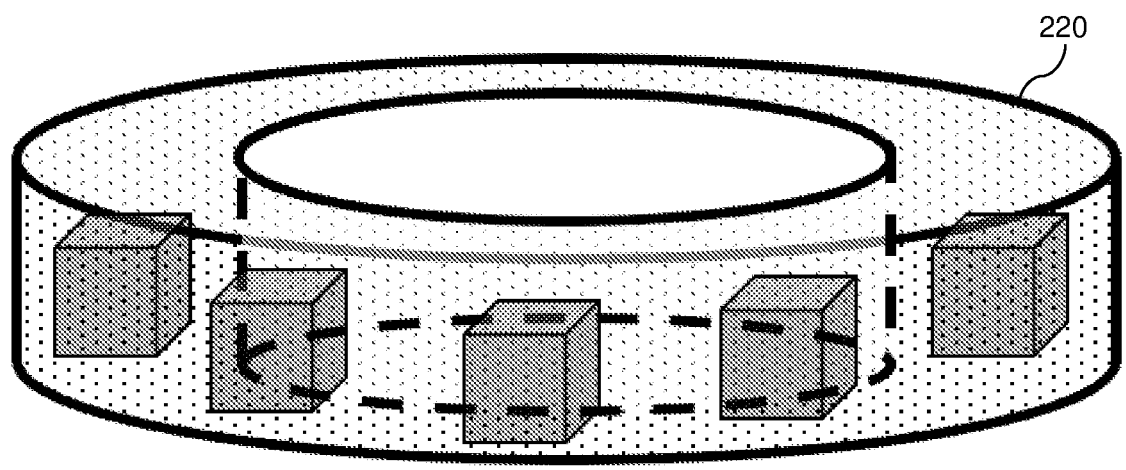
FIG. 4 illustrates an embodiment of a priming frame of the handheld probe of the hMPI system in accordance with an embodiment of this invention.
Figure 5:
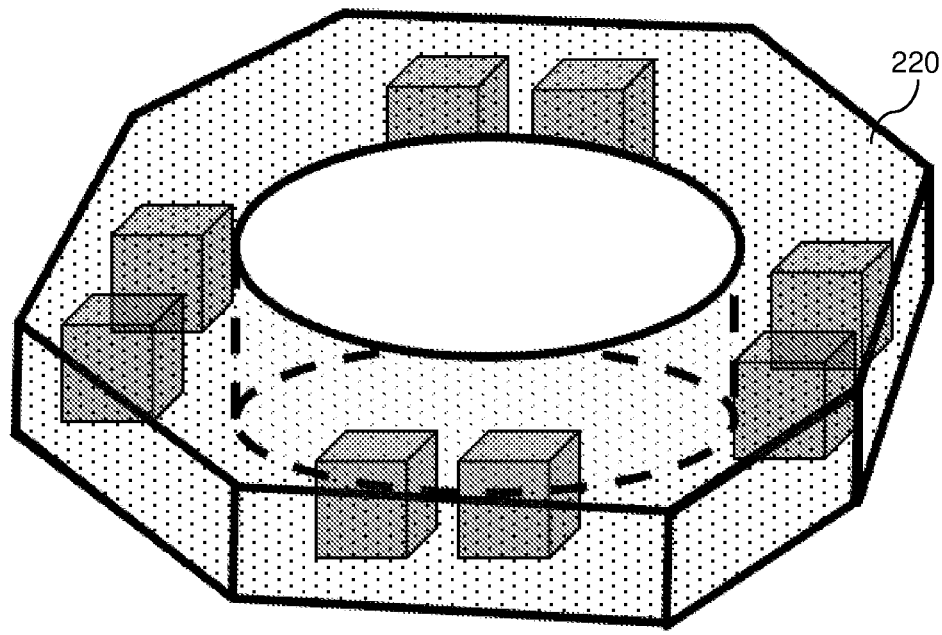
FIG. 5 illustrates another embodiment of a priming frame of the handheld probe of the hMPI system in accordance with an embodiment of this invention.

FIG. 4 shows an embodiment of the arrangement of the magnetic component such as neodymium magnet (NdFeB) evenly distributed around the MPI priming frame 220 which is in a shape of a concentric circle. FIG. 5 shows another embodiment of the arrangement of the magnetic component such as neodymium magnet (NdFeB) evenly distributed around the MPI priming frame 220 which is in a hexagonal shape. FIG. 6 shows another embodiment where the magnetic component forms the MPI priming frame 220. FIGS. 7-14 illustrates the magnetic field verified by experimental Gaussmeter measurement according to various arrangement of the magnetic component in the MPI priming frame 220. One skilled in the art will recognise that other arrangement of the magnetic component may be implemented without departing from the invention. Further, the priming frame be a simple round or square shaped housing with each of the magnetic components being controlled by the processing unit such that the magnetic components are selectively activated according to the embodiments shown in FIGS. 4-6 or other arrangement of the magnetic components as and when desired.

FIG. 7.1 relates to one possible embodiment of the magnet array used for magnetic priming.

FIG. 8.1 relates to another possible embodiment of the magnet array with magnets alternately facing inwards and outwards.

FIG. 9.1 relates to another possible embodiment of the magnet array with magnets all facing inwards.

FIG. 10.1 relates to another possible embodiment of the magnet array with magnets all facing downwards.

FIG. 11 shows larger magnet arrays with magnets all facing downwards. FIG. 12 shows magnet arranged in a border array with magnets alternately facing upwards or downwards. FIG. 13 shows magnet arranged in a cube array with magnets alternately facing upwards or downwards. FIG. 14 shows magnet arranged in another cube array with magnets alternately facing upwards or downwards.

FIGS. 7.2-7.3, 8.2-8.3, 9.2-9.3, 10.2-10.3, 11.2-11.3, 12.2-12.3, 13.2-13.3 and 14.2-14.3 are plots in relation to the magnet array shown in FIGS. 7.1, 8.1, 9.1, 10.1, 11.1, 12.1, 13.1 and 14.1 respectively. Specifically, FIGS. 7.2, 8.2, 9.2, 10.2, 11.2, 12.2, 13.2 and 14.2 plot the z-directional magnetic field at various distances (z-slices) from the priming frame, demonstrating spatial patterning of the magnetic field. FIGS. 7.3, 8.3, 9.3, 10.3, 11.3, 12.3, 13.3 and 14.3 plot the net magnetic field strength regardless of magnetic flux direction demonstrating increased precision when directionality is not required in the imaging algorithm. The magnets represented in FIGS. 7.1, 8.1, 9.1, 10.1, 11.1, 12.1, 13.1 and 14.1 can be permanent magnets or electromagnets. If the magnet is electromagnet, the strength and direction of the electromagnet can be varied to generate a wider range of spatial patterns.

Figure 15:
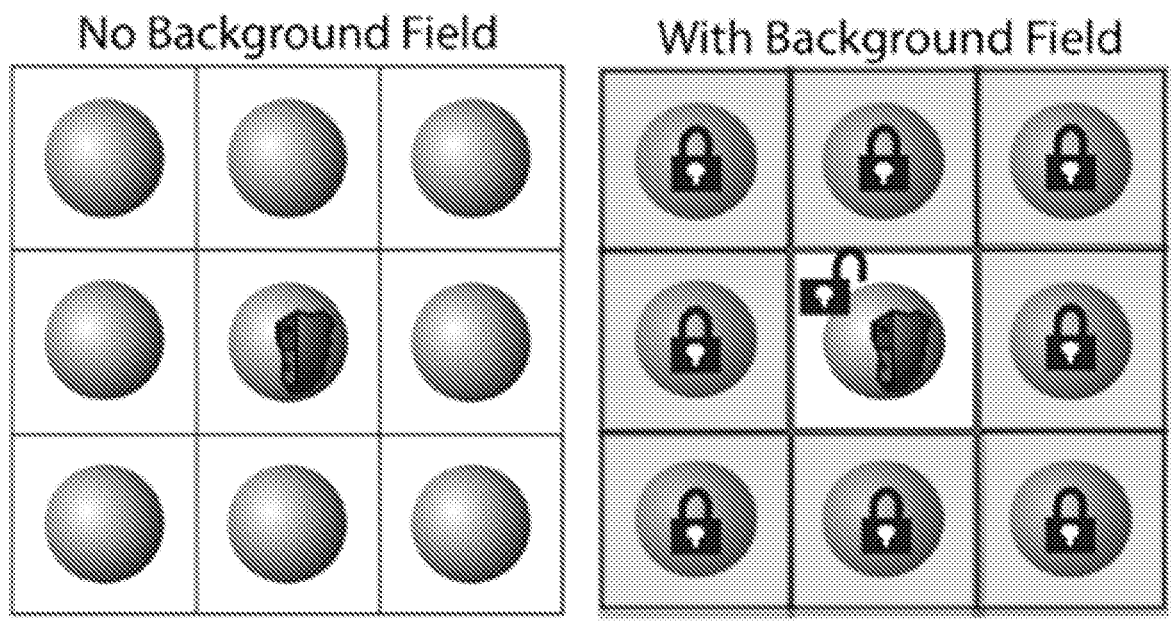
FIG. 15 illustrates the magnetic saturation and priming and voxel selection in accordance with an embodiment of this invention.

FIG. 15 is a conceptual illustration of a 3 by 3 spatial matrix to show how the priming frame generates a background field that affects different nanoparticles located at different locations differently. In this case, the central location is primed to enhance the signal most strongly.

Figure 16:
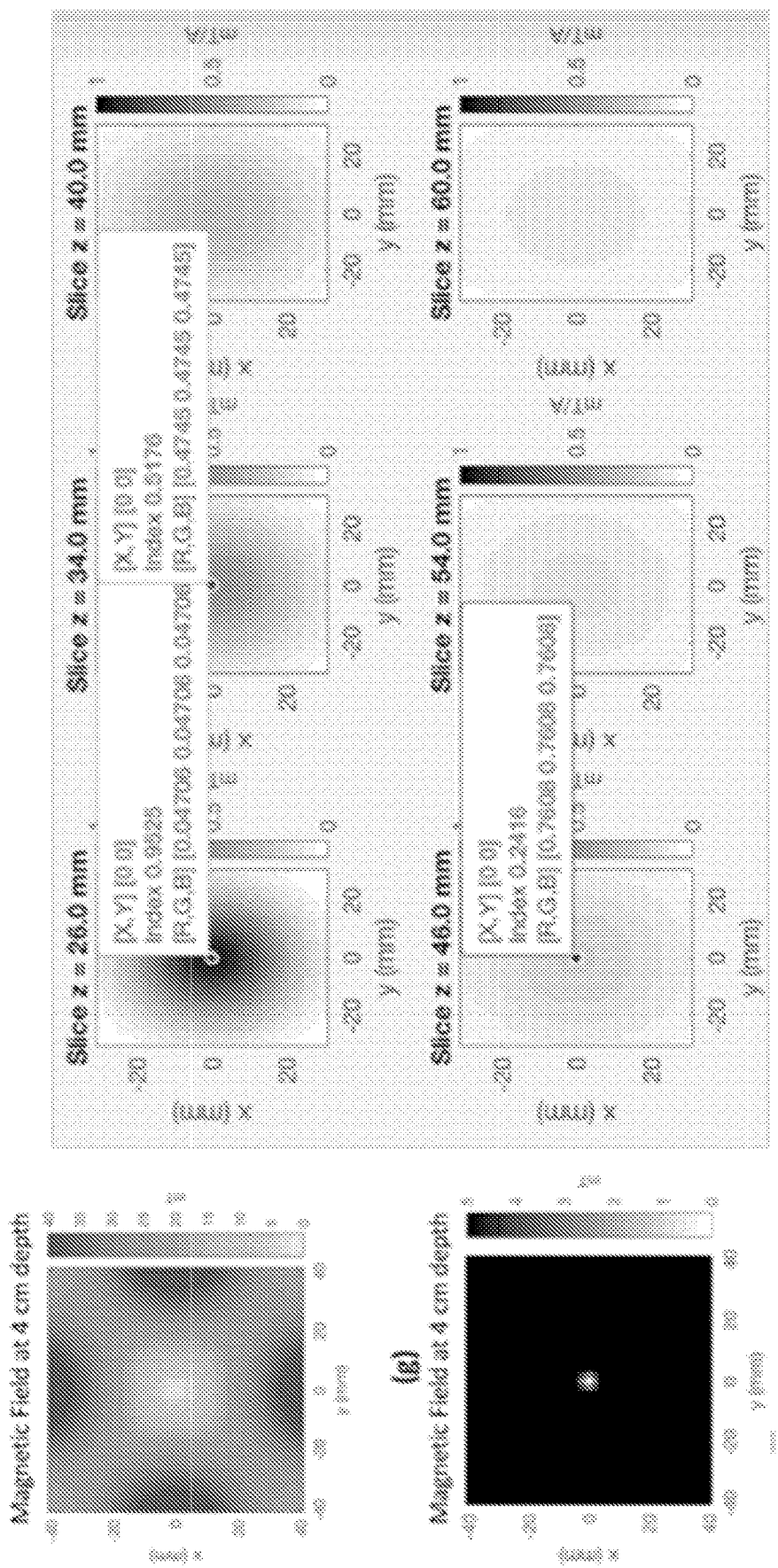
FIG. 16 illustrates using saturation to overcome field inhomogeneity.

FIG. 16 plots two plots of the same magnetic field from priming frame with different color bars. This demonstrates that depending on the "dynamic range of magnetization" of the nanoparticles used, the spatial patterning of nanoparticle magnetization could look very different and it is ideal to tailor the magnetic characteristics of the nanoparticle to be used (as estimated from M-H characterization) to the design of the priming frame.

The MPI transmitter and receiver compartment 240 is configured to house a detection system and a transmitter system. The detection system is arranged proximate the observation region 1710. Rather than detecting signal in the same directional axis as the excitation, the hMPI system can include one or more sensor coils to detect signal in multiple directional axis to aid with spatial encoding and reconstruction.

When exciting the magnetic nanoparticles in the priming frame 220 at the operating frequency, the magnetic sensor coil will also receive the excitation at the operating frequency and this is commonly known as direct feedthrough from transmit to receiver. This creates a problem of swamping the small nanoparticle magnetic signal with the much larger excitation signal.

For feedthrough mitigation, unlike in-bore MPI receiver designs that utilize a gradiometric design, the hMPI system is disadvantaged in the single-sided context, a conventional equal-coil-size gradiometric design will lose significant amounts of signal for a magnetic signal source placed outside of the gradiometer body with greater losses the further the source is away from the sensor body. For in-bore MPI, the magnetic signal source can be placed in one side of the gradiometer and not the other. To address this issue, the hMPI system 100 uses two concentric sensor coils 1721 and 1722 with similar winding but in opposite direction and located within and outside of the transmit coil 1730 which is concentric to the sensor coils 1721 and 1722. The similar winding of both sensor coils 1721 and 1722 means that minimal signal from an externally located magnetic source is wasted, but due to the different magnetic field directions and magnitude of the transmit coil outside and within of itself, direct feedthrough can be mitigated. For example, within the transmit coil 1730, the magnetic flux density is a lot higher than outside the transmit coil 1730. The unequal sensor coil diameter of the external sensor coil 1721 and internal sensor coil 1722 minimizes negation of sensitivity by the two sensor coils 1721 and 1722, especially at-depth where the small diameter internal sensor coil's 1722 sensitivity region cannot reach. In FIG. 19.1, the layout of the external sensor coil 1721 and internal sensor coil 1722 are shown, where the transmit coil 1730 will fit sandwiched in between the external sensor coil 1721 and internal sensor coil 1722. In FIG. 19.2, the sensor sensitivity maps are shown at different image depth (z-axis sensitivity). It is demonstrated that the external sensor coil 1721 dominates the sensitivity map with minimal loss in sensitivity due to the opposite-wound internal sensor coil 1722. The loss is restricted to a central spot and disappears after 10 mm depth. Furthermore, from 0 mm to 10 mm depth, the sensitivity map is inverted at this central spot due to the internal sensor coil 1722. This will invert the nanoparticle signal in a depth-dependent manner along the central magnetic beam, and thus will greatly help in spatial encoding within the beam axis when used in conjunction with abovementioned spatial encoding strategies.

In addition, signal recording strategies of only using the second or third harmonic or fifth harmonic of the magnetic nanoparticle signal can also be used in addition to abovementioned strategies to further mitigate feedthrough.

Figure 17:
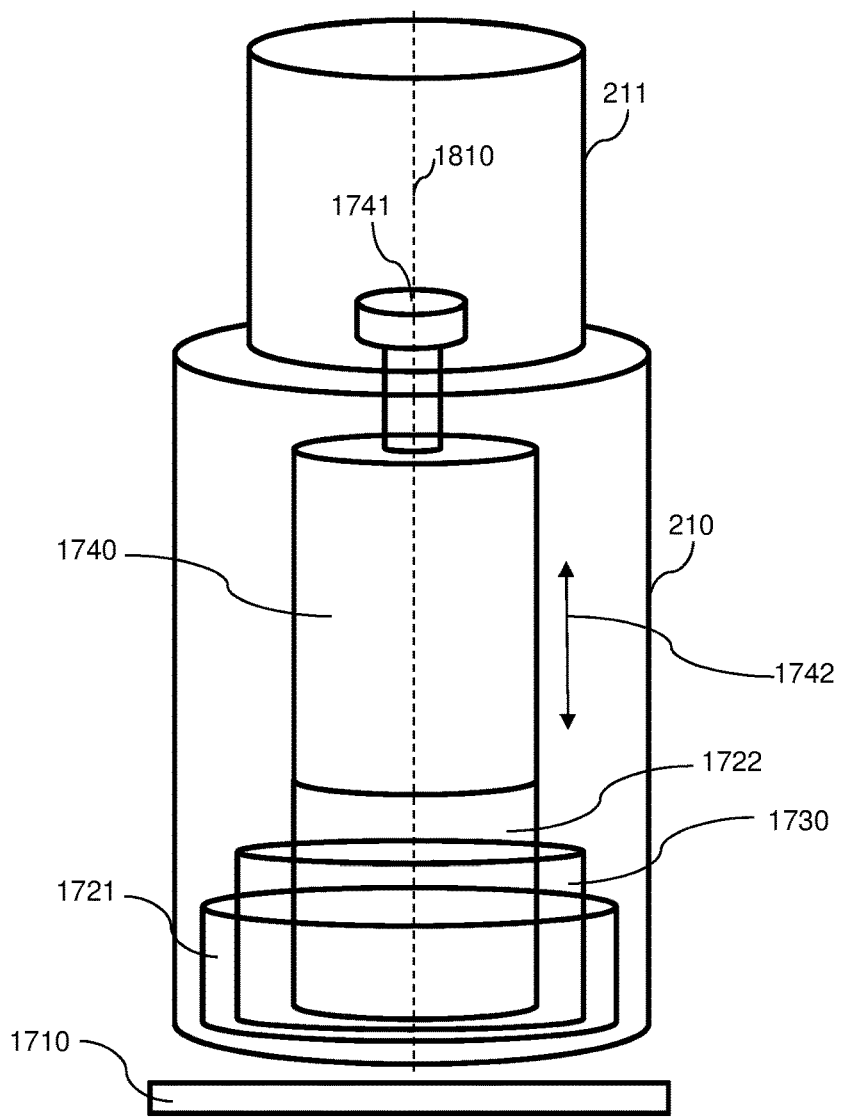
FIG. 17 illustrates the arrangement of the sensor coils and the transmit coil in the handheld probe in accordance with an embodiment of this invention.
Figure 18:
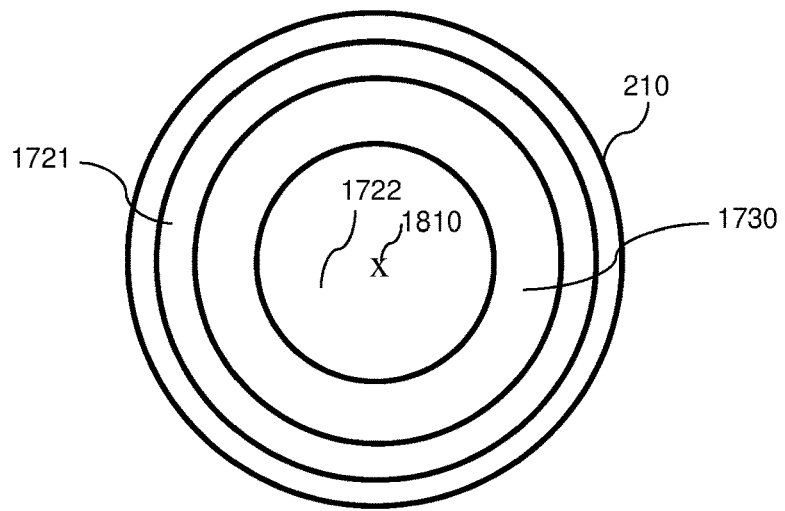
FIG. 18 illustrates a bottom view of the sensor coils and the transmit coil in the handheld probe in accordance with an embodiment of this invention.

To further ensure that the inductive voltage on both sensor coils 1721 and 1722 are equal and exactly out-of-phase, an apparatus 1740 with a thumb screw 1741 is used for fine translation of one sensor coil relative to the transmit coil 1730 to strengthen or weaken the inductive voltage of one sensor coil for fine adjustment purposes. As shown in FIG. 17, the apparatus 1740 with a thumb screw 1741 is adapted to be coupled to the internal sensor coil 1722 for the fine translation of the internal sensor coil 1722. More specifically, the thumb screw 1741 allows movement of the internal sensor coil 1722 in the directions of the arrow 1742 so that the internal sensor coil 1722 moves closer to the probe surface 250 or away from the probe surface 250. For exact out-of-phase tuning, tunable RLC circuits with tunable capacitor or resistor can be added to the sensor circuits.

FIG. 19 illustrates the sensitivity map of the sensor coils 1721 and 1722 while FIG. 20 illustrates the sensitivity map of the transmit coil 1730. FIG. 19.1 and FIG. 20.1 are examples of sensitivity maps of possible embodiments of the sensor and transmit which is tailored to match the imaging depth and imaging field-of-view size the priming frame is capable of. Other than pancake shapes, other possible shapes include conic, semi-birdcage, saddle or butterfly shapes. FIGS. 19.2 and 20.2 plot the z-directional magnetic field at various distances (z-slices) from the priming frame, demonstrating spatial patterning of the magnetic field. FIG. 20.3 plots the net magnetic field strength regardless of magnetic flux direction demonstrating increased precision when directionality is not required in the imaging algorithm.

FIG. 21 is the experimentally measured sensitivity of the device prototype in terms of mass of iron (nanoparticles). The left plot is the signal variation of the device as iron mass is varied and an almost linear relationship is observed, demonstrating that the device design is capable of direct quantification of iron mass. The right plot is data from a standard in-vitro laboratory Prussian Blue colorimetric (absorbance) assay for iron content. The corresponding noise floor for the device and assay are indicated by the dashed horizontal lines. This is plotted to demonstrate that sensitivity and quantitative nature of the imaging device is comparable to standard laboratory assays.

Returning to FIG. 3, the MPI transmitter and receiver compartment 240 is housed within the main housing 210 which has a convex probe surface 250 to produce a conic one-sided field-of-view 260 similar to ultrasound as opposed to "within-bore" field-of-view of full-bore MPI scanners or "flat pancake" field-of-view of single-sided MPI. Acquisition of the conic field-of-view sweeps the "magnetic beam" to cover the conic volume as facilitated by the slightly convex surface of the hMPI handheld probe 150.

The 3D position and direction of the "magnetic beam" is recorded by the sensor coils 1721 and 1722 with gyroscopic and optical translation sensors in the hMPI handheld probe 150. The parameters of these sensors are critical in subsequent image reconstruction based on the magnetic signal recorded from hMPI transmit receive components. Some ideal specifications are as follows. For the optical translation sensor, optical resolution better than 1600 dpi and refresh rate of above 6000 samples per second corresponding to at least 15 kHz operating frequency with 20% duty cycle would be ideal. For the gyroscopic sensor, angular rate measurement better than ±100 degrees per second in all 3 cartesian axes with bias stability of lower (better) than 1 degrees per hour.

The parameters of these sensors are selected for the purpose of aiding in digital recording of the magnetic beam position and tilt which is one of the key objectives.

Existing prior art uses heavy-duty electromagnets to rapidly shift the magnetic field in 3D-space, and calculates the magnetic field position from the electromagnet parameters. Conversely, the embodiment of this invention generates a fixed known magnetic field in beam shape, and utilizes gyroscopic and optical translation sensors to measure the beam position for image reconstruction. This means that the hMPI system 100 gyroscopic and optical translation sensors. The optical translation sensor which may be a complementary metal oxide semiconductor (CMOS) image sensor may be arranged at the probe surface 250 and in the middle of the internal sensor coil 1722. Alternatively, optical fiber is piped through the internal sensor coil 1722 and along the vertical axis 1810 (avoiding cross-talk with the magnetic components in the internal sensor coil 1722) so that light is received from the piped optical fiber directed to the CMOS image sensor located away from the probe surface 250.

To measure the beam tilt, one embodiment would be to place the gyroscope along the vertical axis 1810 of the hMPI probe in order to sense tilt when the probe is conically tilted to interrogate a conic field-of-view. To measure the lateral translation in the x-y plane, the ideal location would be along the vertical axis of the hMPI probe and approximately at the bottom surface and in the middle of the internal sensor coil 1722. Alternatively, to make space for other components, the gyroscopic sensors could also be placed away from the vertical axis. In this embodiment, the gyroscopic sensors will need to be located at least two positions on the outermost radial positions from the hMPI vertical axis, which in this particular embodiment would be at the edges of the priming frame 220. Two positions will allow tracking of lateral translation while compensating for any erroneous rotation about the vertical axis of the handheld probe 150.

The handheld design as opposed to conventional in-bore MPI and "moving-table" MPI enables easy coupling with other modalities without the need for engineering integration of the hardware of the two modalities. This enables handheld probe 150 to be easily used in conjunction with existing established research tools already found in typical laboratories. For example, conventional bioluminescent/fluorescent preclinical in vivo imaging systems i.e. IVIS spectrum/lumina uses a top-down illumination and sensing where the rodents-to-be-scanned can be placed up to 5 in parallel on a stage. The chamber typically has much vertical empty space. This can be exploited by handheld MPI where due to its lightweight handheld nature with top-down scan, it can scan the same rodents with MPI via a support stage put above the rodents as shown in FIG. 22.3 without disturbing or moving the rodents out of the IVIS stage, thereby avoiding any re-positioning confounds/artifacts. We provide a sample MPI image where the MPI signal is overlaid onto the top-down photo of the animal stage to show compatibility with the IVIS imaging concept, where there is fluorescent/bioluminescence overlay on a top-down photo as well. In contrast, in-bore or moving table MPI have to physically transport the rodents into another scanner which is likely to create positioning problems that hamper accurate multi-modal image overlay. Another example is combining with small footprint cabinet X-ray units. The same concept can be applied where after the X-ray scan, the MPI handheld scan can be done via a support stage put above the rodents as shown in FIG. 22.3 without disturbing or moving the rodents The depth-of imaging using the handheld probe 150 is approximately up to 4 cm and this is much better than known art which is approximately 1 cm. The depth-of imaging of approximately 4 cm is due to the arrangement and configuration of the priming frame, transmitter coil and sensor coils.

Figure 23:
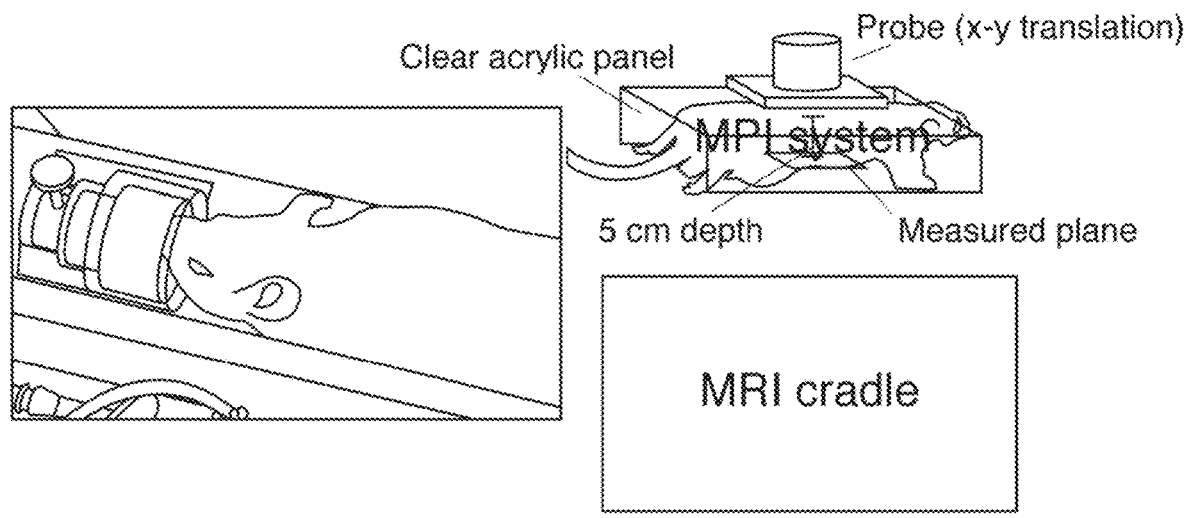
FIG. 23 illustrates a first anatomic reference strategy in accordance with an embodiment of this invention.

Trial results of the hMPI system 100 have shown good detection sensitivity of clinical-grade and functionalized magnetic nanoparticles. FIGS. 22 and 23 illustrate the arrangement of a test subject for performing the trial. FIGS. 22.1 and 22.2 illustrate the arrangement of the handheld probe 150 placed on top of a panel such as a clear acrylic panel with a test subject (in this case, a mice) within the clear acrylic panel. In this arrangement the measured plane can either be 1 cm depth as shown in FIG. 22.1 or 4 cm depth as shown in FIG. 22.2. FIG. 22.3 shows an image of a rodent with positive control nanoparticle injected by tail vein. Based on the information collected from the handheld probe 150 comprising image from the optical sensor, data from both sensor coils 1721 and 1722, the hMPI system 100 is able to translate the information to the image as shown in FIG. 22.3. Specifically, the nanoparticle injected to the rodent can be accurately captured.

While FIG. 22.3 illustrates a two dimensional image, this invention implements a spatial encoding strategy to provide information on the 3rd dimension of the imaging field-of-view. Existing prior art using tomographic rotate-around-the-imaged-object methods with Radon transform to extract this 3rd dimension. The hMPI system 100 in accordance with this invention enables a handheld probe 150 which does not require rotate-around-the-imaged-object to provide information on the 3rd dimension of the imaging field-of-view. The details of the spatial encoding strategy are provided above in section that details "Spatial encoding within the beam itself is performed by the difference . . . ". Essentially, spatial encoding within the axis of the magnetic beam provides this information while conventional tomographic methods such as CT cannot discern positioning within their beam and require "rotate-around" scan sequences and Radon transform for image reconstruction.

FIG. 23 illustrates one example of preparing the mice when using the handheld probe 150. Specifically, the mice is placed on an imaging bed with fiducial FOV edge markers to co-register MPI and MRI or PET/MR images. The mice will remain anaesthetized between scans as MPI is portable and can be brought to the MRI or PET/MR scanner. As mentioned above, the trial results of the hMPI system have shown good detection sensitivity of clinical-grade and functionalized magnetic nanoparticles when compared to MRI and PET scan.

Figure 24:
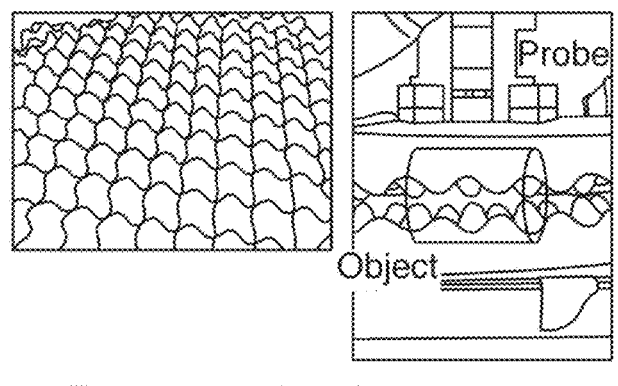
FIG. 24 illustrates a second anatomic reference strategy in accordance with an embodiment of this invention.

FIG. 24 illustrates another example of preparing a test subject for using the handheld probe 150. In this example, memory foam with fiducial marks may be provided covering the test subject. The memory foam is invisible to MPI and hence the 3D reconstruct of the test subject would not be affected by the memory foam. Essentially, the preparation of the test subject as shown in FIGS. 23 and 24 is to immobile the test subject before scanning the test subject with the handheld probe 150.

While FIG. 3 illustrates an embodiment of the hMPI system 100 with a handheld probe 150 with a convex probe surface 250 to be pressed against the subject's body/skin, one skilled in the art will recognise that the same hMPI acquisition, scanning and image reconstruction principles can be applied to handheld probe of different geometries and not just a convex-shaped probe without departing from the invention.

Specifically, the hMPI system 100 can be used for different diagnosis. One possible embodiment of the probe surface 250 of the handheld probe 150 is a breast probe shaped like a cup that is tilted in different angles encompassing the volume of the breast to cover the imaging field-of-view of the entire breast volume. Another embodiment the probe surface 250 of the handheld probe 150 is like a clamp shape holding both sides of the breast.

Another possible embodiment of the probe surface 250 of the handheld probe 150 is a head probe shaped like a cup/helmet that is the tilted in different angles encompassing the volume of the head to cover the imaging field-of-view of the entire head volume.

Another possible embodiment of the probe surface 250 of the handheld probe 150 is an abdomen imaging semi-circular arch encompassing the abdomen volume where the hMPI probe is tilted/translated along the arch to cover the imaging field-of-view of the entire abdomen.

Another possible embodiment of the probe surface 250 of the handheld probe 150 is a rectal-inserted prostate imaging probe in the same shape as ultrasound prostate probe where the hMPI probe is translated along the inserted tube to image a 2D slice of the prostate (similar to ultrasound 2D conic section).

Another possible embodiment of the probe surface 250 of the handheld probe 150 is to perform therapeutic magnetic heating by swapping out the modular probe head for a heating therapeutic hMPI probe. The hMPI heating probe is similar to the hMPI imaging probe 150 described above with a similar "magnetic beam" concept. The difference would be the use of higher excitation frequencies for heating. Due to the use of a "magnetic beam" concept and by magnetic saturation of nanoparticles outside of the beam, the hMPI probe 150 can localize therapy and heating to just the target beam location/line. This is important for precise therapy while sparing healthy tissue from damage.

The hMPI system can receive magnetic signal from the magnetic nanoparticles to be heated in order to have real-time feedback on the thermal dose and microenvironment status such as, but not limited to, temperature, pH and viscosity in the vicinity of the targeted magnetic nanoparticles so as to measure the tissue ablation status of for example, a tumor with magnetic nanoparticles bound to it.

The heating excitation may not be limited to monotonous sinusoidal excitation, and can be amplitude-modulated, frequency-modulated or of an arbitrary function waveform to achieve different excitation harmonic profiles to stimulate the biology or physiological environmental in different ways thermally to affect differing desired biological responses. For instance, neurons may respond to only certain frequency ranges or certain shaped pulses etc.

Another possible embodiment of the probe surface 250 of the handheld probe 150 is to perform magnetic steering of catheters or other interventional surgical instruments through the use of temporally-modulated magnetic forces via its excitation electromagnet and static magnets. The handheld motion of the hMPI probe can also help pull or push catheter tip/surgical instrument tips to navigate through the body. Real-time imaging acquisition and reconstruction using the hMPI system can also be performed for real-time hMPI image-guided steering of abovementioned instruments or catheters.

Figure 25:
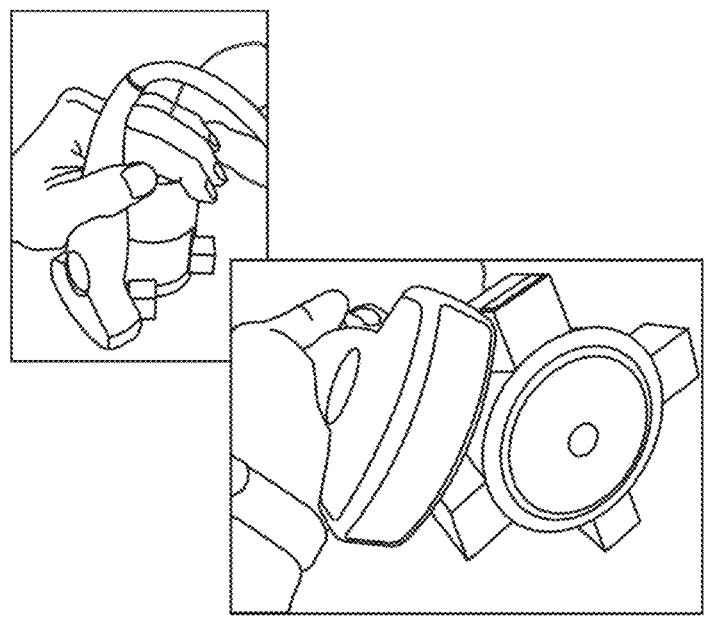
FIG. 25 illustrates coupling an ultrasound to the handheld probe in accordance with an embodiment of this invention.

As mentioned above, ultrasound control and receiver 160 may be added as shown in FIG. 25. Essentially, an ultrasound scanner may be adjacently coupled to the handheld probe 150 to provide the anatomic reference. Alternatively, the housing of the handheld probe 150 may include a mount so that the ultrasound scanner can be adjacently coupled to the handheld probe 150 via the mount. Some anatomic reference strategies that can be adopted include Real-time image rendering like ultrasound, Sections on magnetic nanoparticle tracer, Sections on applications on cancer screening in general, Esophageal cancer screening, Screening of atherosclerotic plaque, Imaging of liver tumors through "negative contrast MPI", and Imaging of adoptive cell therapy and associated benefit (heating for teratoma etc).

Figure 26:
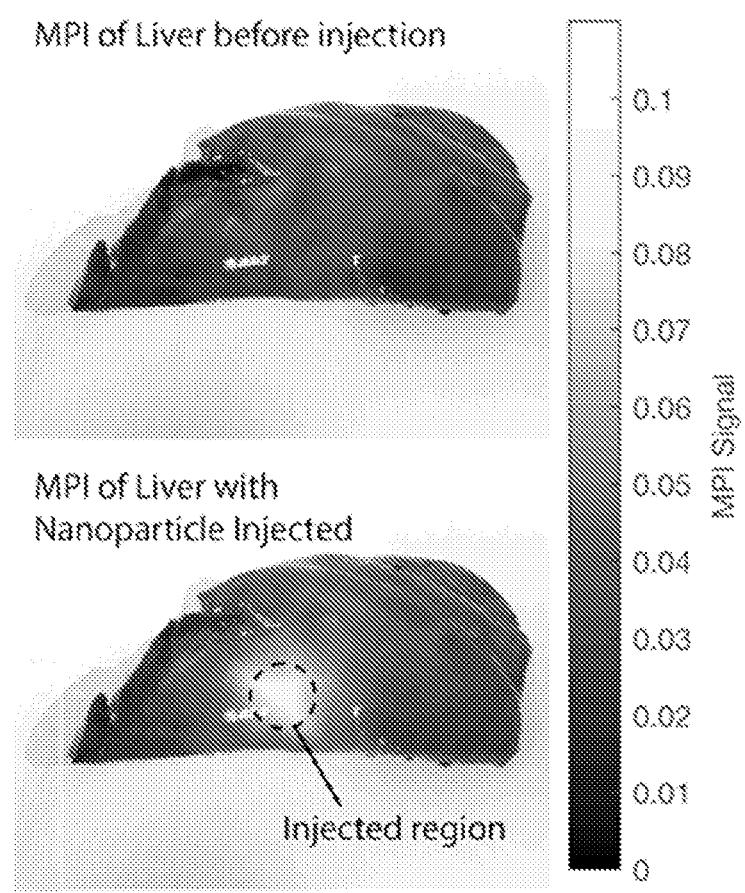
FIG. 26 illustrates a test result of using the hMPI system in accordance with an embodiment of this invention.

FIG. 26 illustrates another trial when nanoparticle is injected to a liver. The top image of the liver show the MPI result before injection of nanoparticle while the bottom image of the liver show the MPI result after injection of nanoparticle. As shown in the bottom image of the liver, nanoparticle can be observed as marked by the circle. This trial demonstrates that the hMPI device only records signal from iron oxide nanoparticles and does not suffer from large background tissue signals even in iron-rich organs such as the liver.\

A final screening may still require MRI or PET/MR scanner. However, before the actual screening via MRI or PET/MR scanner, the subject may first be scanned using the hMPI in accordance with this invention to reduce cost.

The hMPI system 100 is modular and can be placed on a portable trolley with compartments for housing the power amplifiers and signal receive circuits of the hMPI system 100. An array of different handheld hMPI probes each suited to a different body part to be imaged or for different imaging contexts can be implemented with a mountable adapter for receiving the different handheld hMPI probes 150. The connection terminals can use a range of different connector types such as BNC, banana plug, etc. depending on the ampacity required.

While the invention has been illustrated and described in detail in the drawings and foregoing description, such illustration and description are to be considered illustrative or exemplary, and not restrictive; the invention is not limited to the disclosed embodiments. Other variations to the disclosed embodiments can be understood and effected by those skilled in the art in practising the claimed invention.

The invention claimed is:

1. A portable magnetic particle imaging (MPI) device comprising:
   a handheld probe comprising a main housing housing a first sensor coil, a second sensor coil, a transmitter coil arranged between the first and second sensor coils, and an excitation priming frame housing magnetic components; and
   a processing unit comprising a transmitter communicatively connected to the transmitter coil and the excitation priming frame, and a receiver communicatively connected to the first and second sensor coils,
   wherein the first sensor coil and the second sensor coil are two concentric sensor coils with windings in opposing directions, wherein the transmitter coil is surrounded by the first sensor coil, and wherein the second sensor coil is surrounded by the transmitter coil.

2. The portable magnetic particle imaging (MPI) device according to claim 1, wherein the excitation priming frame is in a shape of a circle and the magnetic components are evenly distributed around the excitation priming frame.

3. The portable magnetic particle imaging (MPI) device according to claim 1, wherein the excitation priming frame is a hexagonal shape and the magnetic components are evenly distributed around the excitation priming frame.

4. The portable magnetic particle imaging (MPI) device according to claim 1, wherein the magnetic components are neodymium magnets.

5. The portable magnetic particle imaging (MPI) device according to claim 1, wherein each of the magnetic components is being controlled by the processing unit such that the magnetic components are selectively activated.

6. The portable magnetic particle imaging (MPI) device according to claim 1, wherein the main housing has a convex probe surface.

7. The portable magnetic particle imaging (MPI) device according to claim 1, further comprising an apparatus with a thumb screw adapted for translation of one of the first and second sensor coils relative to the transmitter coil.

8. The portable magnetic particle imaging (MPI) device according to claim 1, wherein the processing unit further comprises a processor, memory and instructions stored on the memory and executable by the processor to:
   receive signals from the receiver; and
   apply spatial encoding to reconstruct the signals to generate a 3-dimensional field-of-view image.

9. The portable magnetic particle imaging (MPI) device according to claim 8, wherein the transmitter is configured to generate a fixed known magnetic field in beam shape for the transmitter coil.

10. The portable magnetic particle imaging (MPI) device according to claim 9, further comprising gyroscopic and optical sensors to measure a beam position for image reconstruction.

11. The portable magnetic particle imaging (MPI) device according to claim 10, wherein the gyroscopic sensor is arranged along a vertical axis of the handheld probe and adapted to sense tilt when the handheld probe is conically tilted to interrogate a conic field-of-view.

12. The portable magnetic particle imaging (MPI) device according to claim 10, wherein the gyroscopic sensor is arranged at two points along a perimeter of the excitation priming frame.

13. The portable magnetic particle imaging (MPI) device according to claim 8, wherein the transmitter is configured to generate a patterned magnetic field for the excitation priming frame.

14. The portable MPI according to claim 1, further comprising:
   an ultrasound control and receiver adapted to provide an anatomic reference.

15. The portable MPI according to claim 14, wherein the ultrasound control and receiver is adjacently coupled to the handheld probe.

16. The portable MPI according to claim 1, further comprising a mountable adapter for receiving the handheld probe.

* * * * *